US008661663B2

(12) United States Patent
Wolfe et al.

(10) Patent No.: US 8,661,663 B2
(45) Date of Patent: Mar. 4, 2014

(54) METHOD FOR MANUFACTURING A MULTIMODAL NEURAL PROBE

(75) Inventors: John C. Wolfe, Houston, TX (US); Wei-Chuan Shih, Houston, TX (US)

(73) Assignee: University of Houston, Houston, TX (US)

( * ) Notice: Subject to any disclaimer, the term of this patent is extended or adjusted under 35 U.S.C. 154(b) by 239 days.

(21) Appl. No.: 13/032,152

(22) Filed: Feb. 22, 2011

(65) Prior Publication Data

US 2011/0208031 A1    Aug. 25, 2011

Related U.S. Application Data

(60) Provisional application No. 61/306,778, filed on Feb. 22, 2010.

(51) Int. Cl.
*H05K 3/02* (2006.01)
(52) U.S. Cl.
USPC ............... 29/847; 29/830; 29/852; 600/378
(58) Field of Classification Search
USPC ............ 29/600, 601, 830, 846, 847, 852; 438/636, 669, 952; 600/373, 378, 393; 607/116
See application file for complete search history.

(56) References Cited

U.S. PATENT DOCUMENTS

| | | | |
|---|---|---|---|
| 5,525,542 A * | 6/1996 | Maniar et al. | 438/669 |
| 6,560,472 B2 * | 5/2003 | Hill et al. | 600/378 |
| 6,887,365 B2 | 5/2005 | Naughton | |
| 7,010,356 B2 * | 3/2006 | Jog et al. | 607/116 |
| 7,282,157 B2 | 10/2007 | Chiba et al. | |
| 7,504,619 B2 | 3/2009 | Wolfe et al. | |
| 7,576,854 B2 | 8/2009 | Wang et al. | |
| 2004/0182707 A1 | 9/2004 | Jardemark et al. | |
| 2006/0017917 A1 | 1/2006 | Cullum et al. | |
| 2006/0038990 A1 | 2/2006 | Habib et al. | |
| 2006/0125033 A1 | 6/2006 | Segal et al. | |
| 2006/0282014 A1 | 12/2006 | Kipke et al. | |
| 2008/0140195 A1 | 6/2008 | Su et al. | |
| 2009/0276923 A1 | 11/2009 | Sumetsky | |

FOREIGN PATENT DOCUMENTS

WO    2006052549    5/2006

OTHER PUBLICATIONS

International Search Report and Written Opinion for PCT/US2011/025701dated Feb. 22, 2011.

(Continued)

*Primary Examiner* — Donghai D Nguyen
(74) *Attorney, Agent, or Firm* — Winstead PC

(57) ABSTRACT

A neural probe includes a probe, wherein a tip of the probe is tapered; an insulating layer covering the probe, and one or more metallic traces, wherein the metallic traces are provide along the length of the probe. The probe also includes one or more contacts provided on the tip of the probe, wherein each of the one or more metallic traces terminates at the one or more contacts, and the one or more contacts provide an array of nanosized metallic pillars. The neural probe may also incorporate a lightguide. The lightguide may include an insulating layer providing a first cladding layer on the probe, a core layer provided on top of the first cladding layer, wherein the metallic traces and contacts are provided in the core layer with a core material, and a second cladding layer provided on top of the core layer.

14 Claims, 20 Drawing Sheets

(56) References Cited

OTHER PUBLICATIONS

"Flexible optitrode for localized light delivery and electrical recording", S.-T. Lin et al, Optics Letters, vol. 37, No. 11, Jun. 1, 2012, pp. 1781-1783.

"Nanoscale Pattern Definition on Nonplanar Surfaces Using Ion Beam Proximity Lithography and Conformal Plasma-Deposited Resist", Dhara Parikh et al, Journal of Microelectromechanical Systems, vol. 17, No. 3, Jun. 2008, pp. 735-740.

"Fabrication of 0.25m surface acoustic wave devices by ion beam proximity printing", D. P. Stumbo et al., Journal of Vacuum Science and Technology, B 9 (6), Nov./Dec. 1991, pp. 2879-2881.

"Neural particle lithography: a simple solution to charge-related artefacts in ion beam proximity printing", J C Wolfe and B P Craver, Journal of Physics D: Applied Physics, 41 (2008) 024007, 12 pp.

* cited by examiner

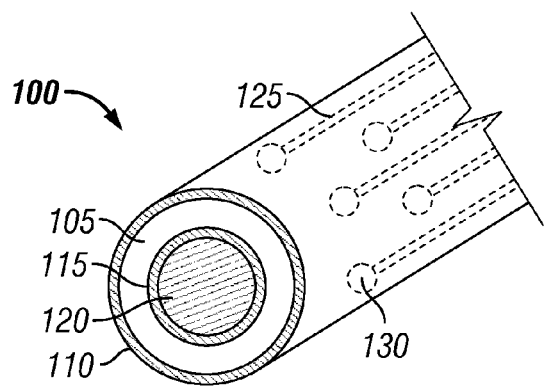
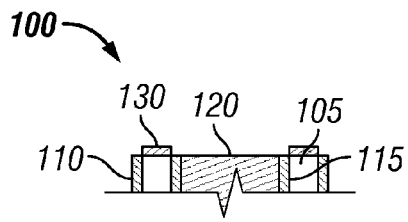
FIG. 7A    FIG. 7B
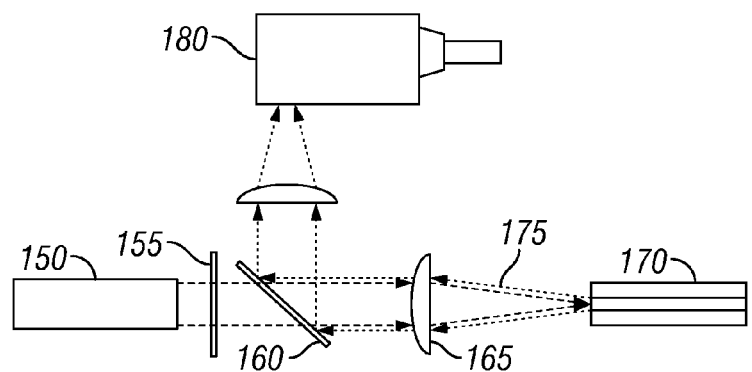
FIG. 8

50 nm

METHOD FOR MANUFACTURING A MULTIMODAL NEURAL PROBE

RELATED APPLICATIONS

This application claims the benefit of U.S. Provisional Patent Application No. 61/306,778 to Wolfe et al., filed on Feb. 22, 2010, which is incorporated herein by reference.

STATEMENT REGARDING FEDERALLY SPONSORED RESEARCH

This invention was made with government support under Grant No. DMI-0521523, Grant No. ECS-0404308, and Grant No. IOB-0517262 awarded by the National Science Foundation (NSF). The government has certain rights in this invention.

REFERENCE TO A SEQUENCE LISTING

Not Applicable.

FIELD OF THE INVENTION

This invention relates to three-dimensional neural probes. More particularly, systems and methods discussed herein are related to multimodal neural probes that can link neuronal electric activity with biochemical changes in the environment near the tip.

BACKGROUND

Brain and spinal cord injuries can have a dreadful impact on the life of an individual. One approach to improving the individual's quality of life is to record brain activity, directly decode an individual's motor intentions, and then use this input to control robotic devices or reanimate the motionless muscles by microstimulation. While the use of brain activity to generate very simple actions has recently be demonstrated, there remain major obstacles that will need to be overcome before these methods can be used for effective therapies in paralyzed humans. One of these problems is the inability of planar probes to provide a 3-dimensional map of local neural activity. Tetrodes, formed by simply twisting 4 wires together and clipping off the end, are thus often preferred in primate studies over planar silicon (e.g. Michigan) probes.

The tetrodes are formed by simply twisting 4 wires together, thermally fusing the insulation, and clipping off the end. The ends may be electroplated to reduce the contact resistance. They have a critical advantage over planar silicon probes in that they can provide a 3-dimensional map of the local neural environment. However, there are many problems with the current technology: 1) electrical characteristics, resistance and capacitance, are not reproducible, 2) resistance is 3 very high-about 300 k$\Omega$ which causes a poor signal-to-noise ratio, 3) the insulation is leaky, 4) they cause significant tissue damage, and 5) the technology is not easily extended to a series of tetrodes at various depths along the shank.

An improved nonplanar multimodal neural probe and fabrication of such a probe that improves the reliability of tetrodes and supports the development of 3-dimensional electrical probes with ten to a hundred channels is discussed herein. The probe provides integrated electrode arrays on the surface of a fine tapered needle that can penetrate the brain with minimum damage. One way to reduce the contact resistance is to increase the area of contact without increasing the physical size of a contact. For example, a dense array of high aspect ratio gold pillars may be fabricate on the contact.

The improved nonplanar multimodal neural probe incorporates a surface enhanced Raman scattering (SERS) sensor at the probe's distal end. This may allow the probe to, for the first time, link the underlying neuronal electrical activity with the associated changes in the biochemical microenvironment near the probe tip. The neuronal activity is modulated by the local biochemical environment, and at the same time, the activity releases neurotransmitters and initiates cascades that change the local environment. An integrated lightguide on the side of the probe may deliver excitation light to the distal end of the probe and return Raman scattered light to a spectrograph-detector assembly outside the brain. A high-density array of gold columns may be fabricated at the lightguide exit and provide surface enhancement.

SUMMARY

In one implementation, a neural probe includes a probe, wherein a tip of the probe is tapered; an insulating layer covering the probe, and one or more metallic traces, wherein the metallic traces are provide along the length of the probe. The probe also includes one or more contacts provided on the tip of the probe, wherein each of the one or more metallic traces terminates at the one or more contacts, and the one or more contacts provide an array of nanosized metallic pillars.

In another implementation, a method for manufacturing a neural probe includes the steps of forming a neural probe, wherein a tip of the neural probe is tapered; coating the neural probe with a first coating to form a first cladding layer, wherein the first cladding layer insulates the neural probe; and coating the first cladding layer with a metal layer; coating the metal with a first resist layer. Next, a stencil mask is aligned with the neural probe and the first resist layer is exposed to form a mask pattern, wherein unexposed resist is removed with a developer. The method further includes removing unmasked metal with an etchant, wherein unremoved metal forms one or more metallic traces; coating the neural probe with a second resist coating to form a second cladding layer; and aligning a first fine wire mask with the probe and exposing the second resist coating, wherein exposed resist is removed with a developer to expose a portion of the metallic traces, and the exposed portion of the metallic traces forms one or more contacts.

In yet another implementation, a neural probe with an integrated lightguide is provided. The neural probe includes a probe, wherein a tip of the probe is tapered; a first cladding layer on the probe, wherein the first cladding layer insulates the probe; and one or more metallic traces provided on the first cladding layer, wherein the metallic traces are provide along the probe. The probe may also include one or more contacts provided on the tip of the probe, wherein each of the one or more metallic traces terminates at one of the contacts; a core layer provided on top of the first cladding layer, wherein the metallic traces and contacts are provided in the core layer; an array of nanosized metallic pillars provided on each of the one or more contact; and a second cladding layer provided on top of the core layer.

The foregoing has outlined rather broadly various features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIGS. 7A and 7B are illustrative implementations of a lightguide;

FIG. 8 is an illustrative implementation of a Raman spectroscopy instrument;

DETAILED DESCRIPTION

Figure 1A:
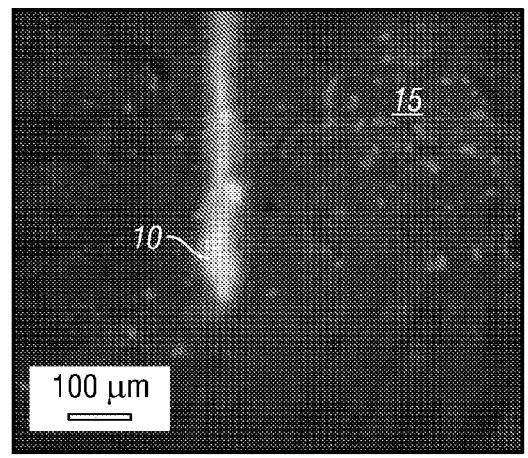
FIG. 1A is an illustrative implementation of a recording tetrode is shown within the ventral tegmental area (VTA) with the DA neurons.

In the following description, certain details are set forth such as specific quantities, concentrations, sizes, etc. so as to provide a thorough understanding of the various embodiments disclosed herein. However, it will be apparent to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing particular embodiments of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

In order to improve neural probes, it is desirable to develop a fabrication technology that improves the reliability of tetrodes and supports the development of three-dimensional electrical probes with ten to a hundred channels. By providing defined integrated electrode arrays on the surface of a fine tapered needle, the probe can penetrate the brain with minimum damage. If the contact resistance of a contact is large, it may significantly degrades the signal-to-noise ratio of the recordings. For example, if the diameter of an electroplated gold contact of a probe is about 15 μm, the contact resistance of the contact is 300-500 thousand ohms. One solution to reduce the contact resistance is to increase the area of a contact without increasing its physical size. For example, an illustrative approach discussed in detail below fabricates a dense array of high aspect ratio gold pillars on the contact.

Another objective is to develop a multimodal probe that will, for the first time, link the underlying neuronal electrical activity with the associated changes in the biochemical microenvironment near the probe tip. The neuronal activity is modulated by the local biochemical environment, and at the same time, the activity releases neurotransmitters and initiates cascades that change the local environment. In particular, a surface enhanced Raman scattering (SERS) sensor may be added at the probe's distal end. Compositional information of the local brain tissue, i.e., a volume ~1000-10000 $\mu m^3$, can be simultaneously obtained by Raman spectroscopy that does not rely on the surface enhancement effect. An integrated lightguide on the side of the probe will deliver excitation light to the distal end of the probe and return Raman scattered light to a spectrograph-detector assembly outside the brain. A high-density array of gold columns will be fabricated at the lightguide exit and provide surface enhancement. In addition to expertise in optical design and instrumentation, extensive chemometric techniques for extracting quantitative information of specific biochemical analytes have been developed.

An approach to fabricating the electrical contact, integrated lightguide, and SERS nanostructures is atom beam proximity lithography where a stencil mask is illuminated with a broad beam of energetic helium atoms and transmitted beamlets transfer the pattern to resist on a substrate. The technology, coupled with a unique conformal resistant deposition process, has the unique capability of fabricating nanoscale structures on a needle at distances up to 2.5 millimeters from the mask. The use of neutral particles, instead of ions or electrons, ensures that minute electromagnetic fields will not distort the atom beamlets, whose aspect ratio can exceed 50,000:1. A proven fluorescence-based alignment technique may be used to register the various layers of the integrated probe.

A research group at the Baylor College of Medicine uses in vivo recording techniques to investigate the mechanisms that underlie learning and memory that often takes place beneath our consciousness to shape our behavior. In the example that follows, tetrodes are used to investigate in vivo action potential firing rates of dopamine (DA) neurons in the ventral tegmental area (VTA) of the midbrain.

Figure 1B:
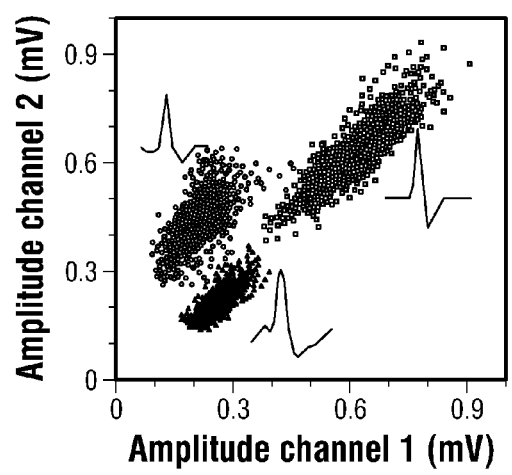
FIG. 1B illustrates isolation of units shown based on the amplitudes of action potential spikes measured on 2 of the 4 channels that make up a tetrode.
Figure 1C:
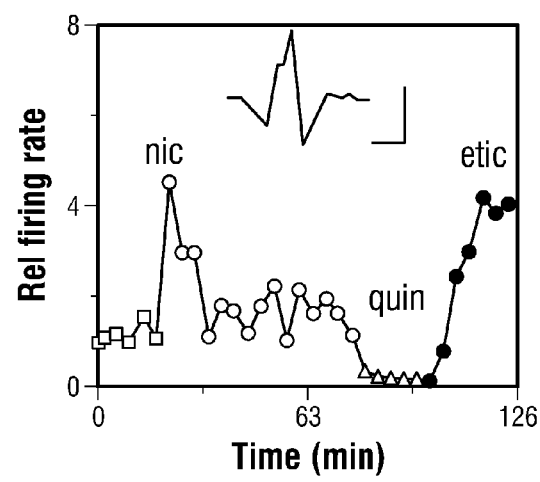
FIG. 1C illustrates an example of the time course of the normalized firing rate of a DA neuron in response to i.p. injection of nicotine (0.4 mg/kg), quinpirole (0.5 mg/kg, a D2 agonist), and eticlopride (0.5 mg/k, a D2 antagonist)

Nicotine (0.4 mg/kg, i.p.) increases the firing of DA neurons in freely-moving rats and mice. FIG. 1A illustrates the track of a recording tetrode 10 (fluorescence from DiI) is shown within the VTA with the DA neurons 15 in blue (fluorescent antibody for tyrosine hydroxylase). FIG. 1B illustrates isolation of units is shown based on the amplitudes of action potential spikes measured on 2 of the 4 channels (wires) that make up a tetrode. The average waveform is shown next to each cluster of spike amplitudes. FIG. 1C illustrates an example of the time course of the normalized firing rate of a DA neuron in response to i.p. injection of nicotine (0.4 mg/kg), quinpirole (0.5 mg/kg, a D2 agonist), and eticlopride (0.5 mg/k, a D2 antagonist). An averaged waveform is inserted above with the scale bars representing 0.5 ms and 0.1 mV.

To characterize the function of midbrain (DA) neurons, we can active them by exogenous application of nicotine (e.g., 0.4 mg/kg, ip). We chronically position tetrodes (4-channel electrodes) into the midbrain DA regions of freely-moving rats or mice. We verify that the extracellular recordings are from the DA region after the experiments by cutting tissue sections and labeling for DA positive neurons with antibodies to tyrosine hydroxylase (indicating DA synthesis). The locations of the tetrode wires are determined by stimulus induced lesions and/or dye painted onto the tetrodes (FIG. 1A). The action potential spikes from multiple individual neurons are isolated from the recordings (FIG. 1B). Multiple criteria are applied to identify units as DA neurons. The units have a relatively low firing frequency (0.5 to 8 Hz), and their spike waveforms are long (>2 ms) and often display complex action potentials previously attributed to DA neurons (inset, FIG. 1C). Based on the literature, D2 receptor pharmacology is used to further support the identification of the units that display the correct firing frequency and waveforms of DA neurons.

When a moderate concentration of nicotine (0.4 mg/kg) is injected intraperitoneally, the DA neuron firing frequency increases (e.g., FIG. 1C). As required for the identification, the D2 agonist, quinpirole (0.5 mg/kg, ip), decreases the spike firing rate; and the D2 antagonist, eticlopride (0.5 mg/kg, ip), increases the spike firing rate of all the putative DA neurons (FIG. 1C). Another aspect of these in vivo recordings of DA unit activity is to follow the impact of pharmacological drugs used to manipulate neuronal pathways that participate in memory.

Neural Probe Technology

Some conventional tetrodes may be formed by simply twisting 4 wires together, thermally fusing the insulation, and clipping off the end. The ends may be electroplated to reduce the contact resistance. These tetrodes have a critical advantage over planar silicon probes in that they can provide a 3-dimensional map of the local neural environment. However, there are many problems with the current technology: 1) electrical characteristics, resistance and capacitance, are not reproducible, 2) resistance is very high-about 300 k$\Omega$ which causes a poor signal-to-noise ratio, 3) the insulation is leaky, 4) they cause significant tissue damage, and 5) the technology is not easily extended to a series of tetrodes at various depths along the shank.

Figure 2:
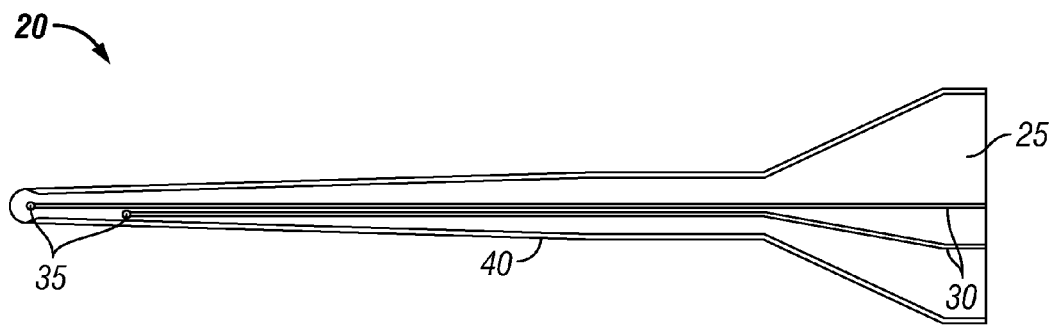
FIG. 2 is an illustrative implementation of a nonplanar multimodal neural probe.

Methods and systems for an improved nonplanar multimodal neural probe are discussed herein. FIG. 2 is an illustrative implementation of a nonplanar multimodal neural probe 20. The probe may be made of a thin, rigid material 25, such as a shape memory alloy, stainless steel, titanium, glass or optical fiber, or any other suitable material. In the illustrative implementations discussed herein, neural probe 20 is made from a shape memory alloy 25 that does not kink. For example, the probe may be formed from nitinol and may be about 4" in length and 50 $\mu$m in diameter. Within 0.2" of the tip, the probe may taper to 25 $\mu$m. An end opposite the tip (not shown), the probe may expand to a diameter 100 $\mu$m or greater to allow the metallic traces 30 on the probe to separate enough to allow individual wires to be bonded to each metallic traces 30. Probes with these specifications are available from Wytech Industries, Ft. Wayne Ind. Metallic traces 30 may run down the probe and terminate at ~15 $\mu$m diameter vias 35 where they contact the cerebrospinal fluid. For example, insulated gold traces or any other suitable traces may run down the probe. This smooth probe should cause significantly less tissue damage than the current tetrodes, which resemble fish spears.

Figure 3B:
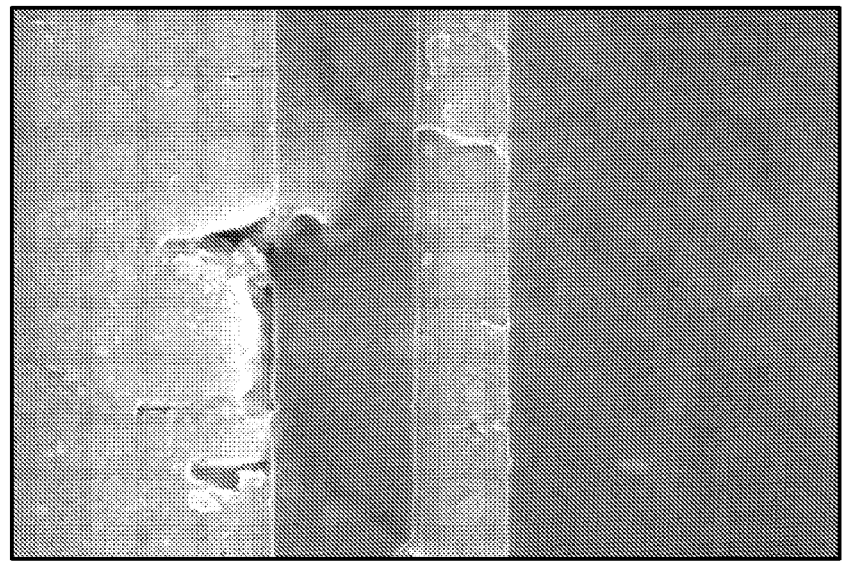
FIG. 3B shows a plasma coating after ion implantation.
Figure 3A:
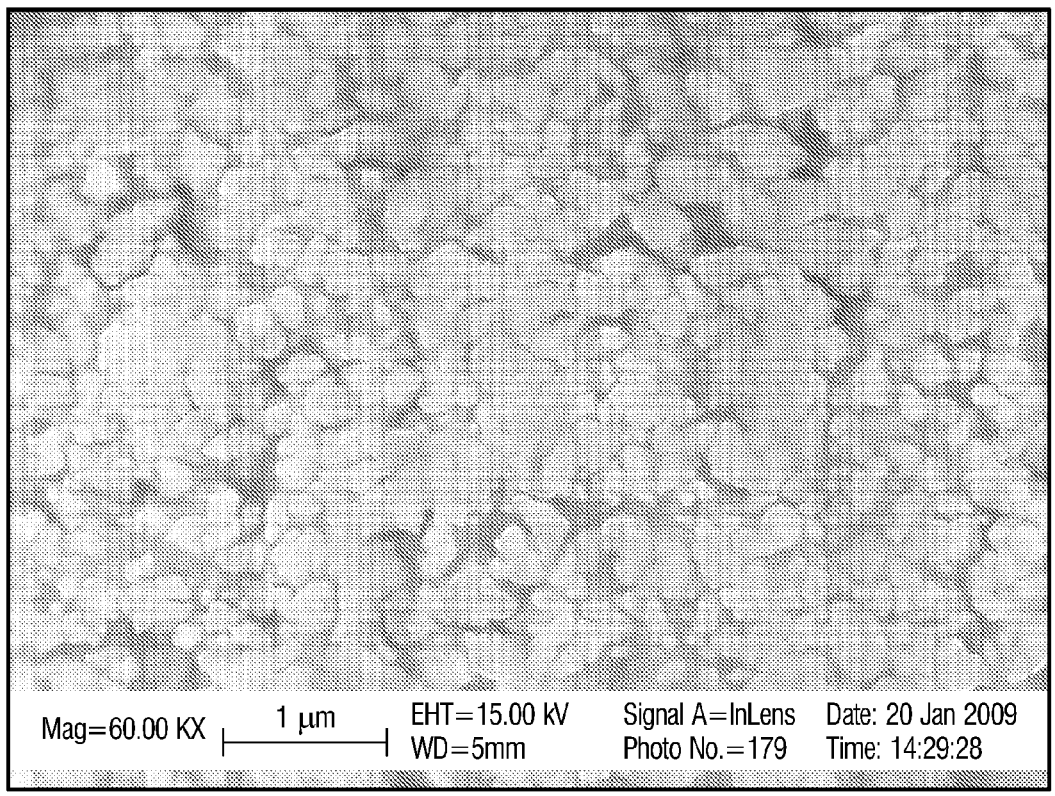
FIG. 3A shows the surface of a 50 μm nitinol wire with ~0.2-0.5 μm roughness.

FIG. 3A shows the surface of a 50 $\mu$m nitinol wire with ~0.2-0.5 $\mu$m roughness. The neural probe may be coated with conformal insulating layer to cover the voids. For example, a robust plasma coating, such as plasma polymerized methylmethacrylate (PPMMA), poly(methylmethacrylate) (PMMA), glass, thermoplastic, or any other combination of one or more suitable materials may be utilized. As shown in FIG. 3B, after ion implantation, the plasma coating is free of pinholes and fills the reentrant cavities on the surface of a rolled tungsten foil. The smooth surface of the coating minimizes tissue damage that may be caused by the neural probe. It also serves as a negative tone resist that can be developed in amyl acetate.

Nanostructured Contact

The magnitude of the 1 kHz impedance between a 15×15 $\mu$m$^2$ smooth gold contact and cerebrospinal fluid is 2-6 M$\Omega$. Electroplated gold can be optimized for high surface roughness, increasing the electrochemically active, or effective, surface area without changing the geometrical area. As a result, the corresponding impedance drops to ~500 k$\Omega$. Although this represents the state of the art in neural recording, it is still too high for low noise recordings.

Figure 4:
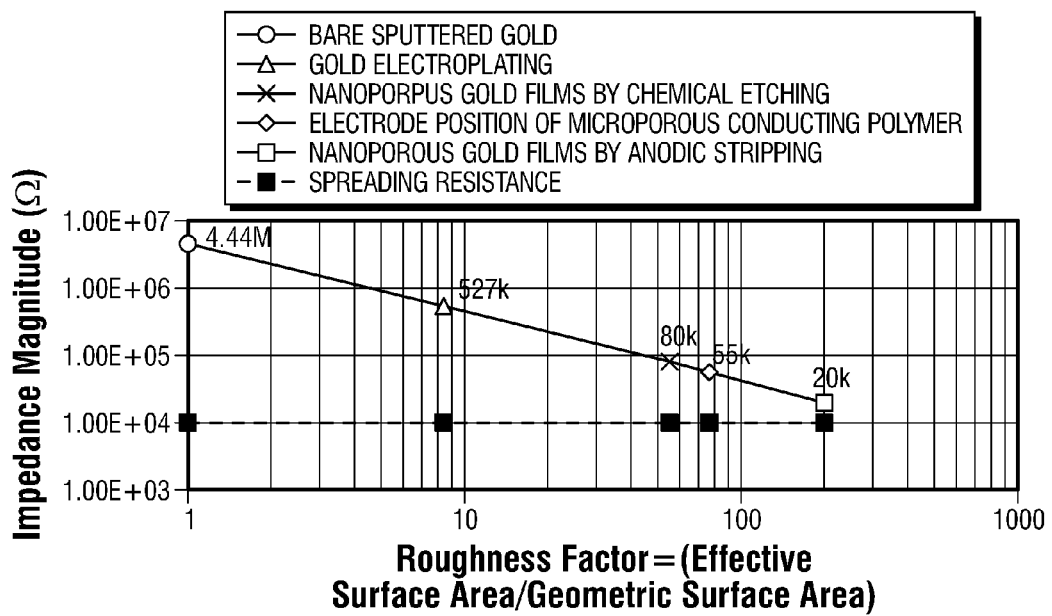
FIG. 4 illustrates a plot of the magnitude of the 1 kHz impedance versus surface roughness factor for different technologies.

There are several other approaches that could further increase the effective surface area. One approach includes the electrodeposition of microporous conducting polymers and the formation of nanoporous gold films using alloying/dealloying processes. The effective surface of these films, which have a 3-dimensional structure with pore sizes in the 10-20 nm range and ligament sizes between 30-60 nm, can approach 200. FIG. 4 illustrates a plot of the magnitude of the 1 kHz impedance of a 15×15 µm² contact versus surface roughness factor (the ratio of the effective to geometrical surface areas) for different technologies clearly shows the inverse relationship between impedance and the roughness factor. As can be seen, nanoporous gold films provide the highest effective surface area and have impedances close to the theoretical limit imposed by the spreading impedance of the contact.

Figure 5A:
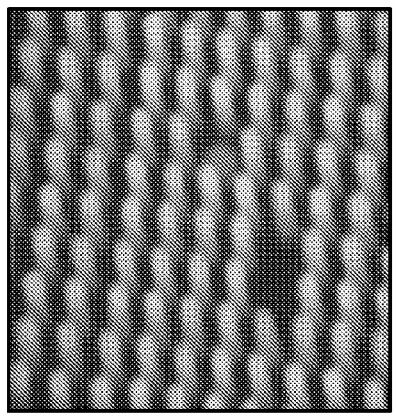
FIGS. 5A and 5B shows an example of a fabricated array of gold pillars.
Figure 5B:
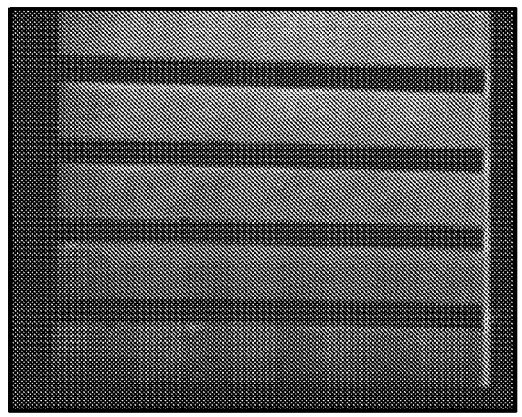
Figure 6A:
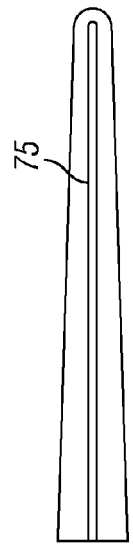
FIG. 6A to 6H are illustrative implementations showing a process flow for forming the conductors and vias.
Figure 6B:
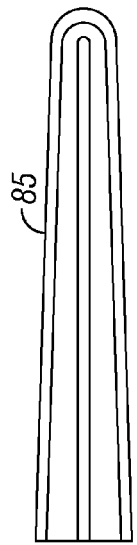
Figure 6C:
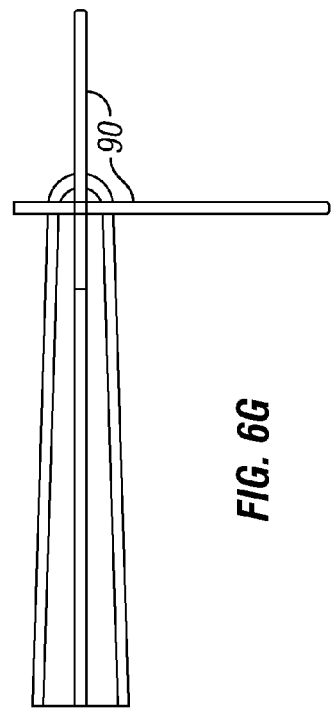
Figure 6D:
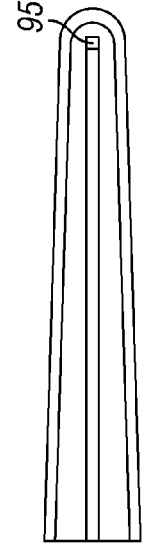
Figure 6E:
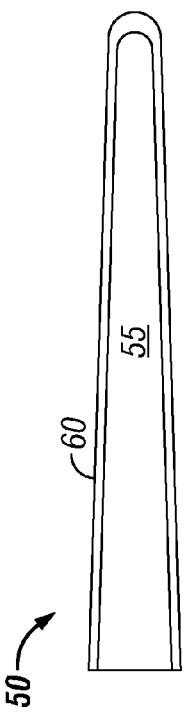
Figure 6F:
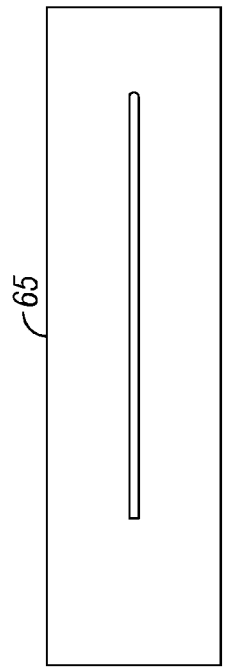
Figure 6G:
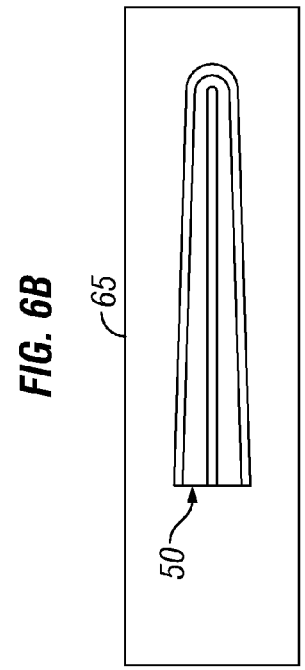
Figure 6H:
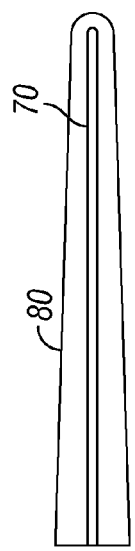

In order to increase the surface area of neural probe contacts, a three-dimensional structure may be provided on each of the contacts. For example, an array of nanosized cylindrical, rectangular, square, conical, or elliptical pillars may be provided on the contacts. However, it will be recognized by one of ordinary skill in the art that other three-dimensional structures, rather than pillars, may be utilized. In an illustrative implementation, the diameter of each of the four contacts at the 40 µm tip of a neural probe may be about 15 µm. The nonplanar multimodal neural probes discussed herein may use a hybrid approach where a controlled array of gold pillars, 50-60 nm in diameter and 300 nm in height on 120 nm pitch, which may be formed by nanolithography and electroplating on each contact pad of the neural probe. This will increase the effective surface area by about 7-10 times over polished gold. FIG. 5A shows an example of a fabricated array of gold pillars, and FIG. 5B shows that areas comparable to those required for contact applications can be fabricated. Surface treatments, including the electroplating of an additional rough film or alloying/dealloying with an aluminum surface coating, may also be provided as means to further increase the effective area. Starting with a well-defined surface structure may significantly improve the repeatability of contact formation.

Process Integration

The monolithic integration of the electrode lines and nanoscale contact structures on the probe substrate is a significant challenge. Part of this challenge is lithography, which must provide nanoscale resolution on substrates with ~0.25 mm height variations. Mainstream semiconductor lithography tools are constrained to ultra-flat surfaces; nanoimprint techniques cannot be used on non-planar or flexible substrates; and the depth of field of focused ion or electron beam lithography tools is severely limited. There are few options for meeting this challenge. One approach is to utilize neutral particle proximity lithography (NPL), as discussed in U.S. Pat. No. 7,504,619 to Wolfe et al., where a broad beam of energetic helium atoms floods a stencil mask and transmitted beam lets transfer the mask pattern to resist on a substrate. It is feasible with such NPL to print noise-free 50 nm features on a probe with a 0.5 millimeter gap between the mask and substrate. The exposure time would be about 4.5 minutes. A conformal, plasma deposited resist process may be utilized to enable nanoscale pattern definition on non-planar surfaces. Other useful tools such as sputter coating and reactive-ion etching are easily transferred to these substrates, provided that they are mounted in suitable holder. A high precision mechanical fixture may be used to position the mask over the wafer. Alignment of the mask/wafer fixture with the beam, which is extremely critical for large mask-to-wafer gaps, can be accomplished using a technique developed where the registration of a barcode alignment mark in the mask with a corresponding fluorescent mark on the probe is detected by a maximum in the fluorescence signal. Another approach would be utilize ion beam lithography (IBL) and increase the size of the metallic traces and/or probe, thereby overcoming potential problems that artifacts from IBL may cause with the neural probe. However, note that increasing the size of a probe may increase the tissue damaged caused by the probe.

FIGS. 6A-6H are illustrative implementations showing a process flow for forming the conductors and vias. The probe needle 50 may be coated with a multi-layer coating, such as a cross-linked PPMMA coating, sputtered gold 55, and PPMMA resist 60 (blue-semitransparent for clarity). A stencil mask 65 for defining resist line 70 may be utilized to form gold trace(s) 75. The stencil mask opening is aligned with the probe needle 50 (mask is semitransparent for clarity) and exposed. Unexposed resist is removed by amyl acetate developer. Then unmasked gold 80 is removed by an aqueous etchant. A second PPMMA coating 85 may then be applied. Two separate exposures are made using orthogonal orientations of a fine wire mask 90. This cross-links the entire second PPMMA coat except for the point where the wires intersect. After development, the probe is coated with an insulating coat except for an opening 95 (via) at the end of the gold trace where electrical contact is made to the cerebrospinal fluid.

Development of Multimodal Probes

Raman and Surface Enhanced Raman Spectroscopy

A multimodal neural probe that obtains simultaneous electrical and molecular information will revolutionize the field of neuroscience and engineering. In addition to the electrical measurements, Raman spectroscopy (RS) may potentially be used for molecular sensing in brain biochemistry. Conventional RS can fingerprint the chemical composition of local brain tissue of a volume ~1000-10000 µm³, while surface enhanced Raman spectroscopy (SERS) can obtain the molecular content of neurotransmitters near a nanostructured surface. RS and SERS arise from fundamentally the same physical process, i.e., Raman scattering, a type of inelastic light scattering due to changes of polarizability during molecular vibration. RS is advantageous over infrared absorption, another vibrational technique, because the excitation and thus the detection wavelengths can be freely chosen. This avoids the limitations in instrumentation, as well as strong water absorption imposed by infrared light (400-4000 $cm^{-1}$, or equivalently 25-2.5 µm wavelength range).

Lightguide Design and Fabrication

Total internal reflection occurs at the interface of two dielectric materials when the incident light is from the material with higher refractive index and the incident angle is larger than a critical angle. The most significant application via this index guiding principle is optical fiber, in which the core material has slightly higher index than the cladding material. Another example is a strip dielectric waveguide in integrated optics, in which a core material can be silicon or silica with air cladding. The dimension of a waveguide is typically determined based on the number of desired propagating modes. For non-imaging short distance applications, a larger core multi-mode waveguide may be utilized to couple more light for better sensitivity. Another design parameter for lightguides is the optical wavelength it is designed for. For biomedical application, near-infrared wavelength enjoys the least amount of tissue elastic scattering and absorption loss, and thus becomes a popular window for optical techniques to gain deeper penetration. In addition, since Raman spectroscopy works by excitation via a narrow-band source (e.g. a laser), and collection of redshifted light, there is a window of wavelength propagating in the waveguide, from the laser wavelength to the high-energy molecular vibrational transition, which typically covers ~150 nm in the near-infrared wavelength with 785 nm excitation.

FIGS. 7A and 7B are illustrative implementations of a lightguide 100. The lightguide 100 may be the core 105 area sandwiched by two cladding layers 110, 115. The shape of the lightguide 100 is similar to the wall of a capillary tube, wrapping around probe 120 or the Nitinol probe discussed previously. All the optical layers including the core 105 and two claddings 110, 115 may be formed using dip coating of spin-on-glass. The cladding 110, 115 may be a glass with slightly lower refractive index than the core material, thus enabling total internal reflection. The exact refractive indices are design parameters that determine the effective numerical aperture of the lightguide. Core 105 of the lightguide 100 may include metal wires 125 that terminate at a nanostructure 130. After the glass layers are formed, the distal end of the probe will be—flattened, followed by NPL and metallization of gold nanostructures (as shown in FIG. 5). Comsol, a multiphysics finite element simulation software, can be employed in design and optimization of the lightguide. In another implementation, an optical fiber may be utilized as a probe 120 and may also operate as the lightguide. Using the optical fiber as probe 120 obviates the need for a core 105 since the optical fiber may be used as the lightguide. The optical fiber may include a single cladding layer 115. Metal wire 125 and nanostructures 130 may be formed on cladding layer 115, and the metal wire 125 and nano structures 130 covered with an insulating layer rather than a second cladding layer 110.

The nonplanar multimodal probe uses a single optical path, unlike most other existing probes in which different lightguides are employed for excitation and collection. Some light guides provide a laser clean-up filter that is typically mounted at the tip of the excitation arm, while a notch filter which blocks the laser light is at the tip of the collection arm. The laser filter prevents silica Raman signal generated in the excitation arm from entering the sample, and the notch filter prevents the laser light from entering the collection arm. As a result of these filters and at least two multimode optical fibers are needed, the probe becomes very bulky, on the order of millimeters.

In the nonplanar multimodal probe design, the focus is on the high-wavenumber, i.e., >1200 cm$^{-1}$, because the silica Raman and fluorescence from impurity in the lightguide and the tissue decrease rapidly toward the high wavenumber region. For SERS measurements, on the other hand, the silica Raman signal and fluorescence will not be an issue because the SERS signal intensity is at least comparable to them if not stronger. Depending on the exact signal level, the acquisition of RS and SERS signals can be either simultaneous or performed separately.

Customized Raman Spectroscopy Instrument

Excitation laser light ($\lambda_{ex}$) is coupled into the proximal end of the probe and travels to the distal end that is immersed in a measuring site. Raman and/or surface enhanced Raman scattering will be collected depending on if there are nanostructures in place. Note that the returned light has a wide-band frequency content, and is red-shifted relative to the excitation laser. The customized Raman spectroscopy instrument consists of three branches: light delivery, light splitting/coupling, and light collection/detection. FIG. 8 is an illustrative implementation of a Raman spectroscopy instrument. A laser 150, such as a near-infrared (785 nm) diode laser, is employed as the Raman excitation source. After laser-line filtering 155 and a 45°-dichroic filter 160, the laser output is focused by a lens 165 into the lightguide. The same lens collects the counter-propagating SERS signal that emits from the left-end of the lightguide. Since the dichroic filter is designed to pass only at the laser wavelength, it serves as a mirror for the SERS light 175 and redirects it into a spectrograph 180 to be.

RS for Blood Analyte Sensing

Figure 9:
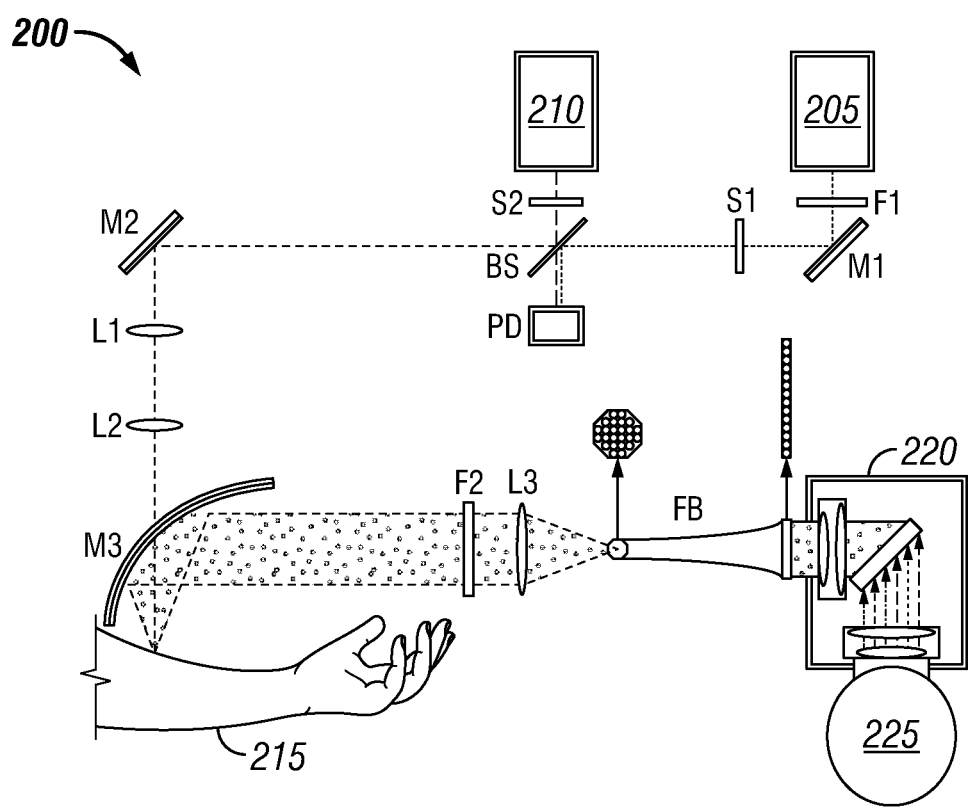
FIG. 9 is an illustrative implementation of a Raman instrument.

Recently, it has been shown that it is feasible to measure concentrations of blood analytes such as glucose transcutaneously via Raman spectroscopy coupled with multivariate calibration. The Raman instrument utilized was designed to achieve extreme throughput. Simulations suggest 30% of all photons emerged from a turbid medium are collected. This was achieved by determining spatial and angular distributions of the Raman signal from turbid media via experiments and Monte Carlo simulations. The instrument employs an off-axis, gold-coated half-paraboloidal minor (Perkin-Elmer) as the collection optic, the specifications of which (f=15.9 mm, collection half-angles 46°/30°, resulting in an effective N.A. of 0.5) were determined by an optical design software (Zemax). In addition to the Raman spectroscopy capability, we have included diffuse reflectance spectroscopy. FIG. 9 is an illustrative implementation of a Raman instrument 200. The prototype bi-modal Raman and diffuse reflectance instrument (FIG. 9) employs laser 205, such as a 830 nm diode laser from Process Instruments Inc., as the Raman excitation source and a lamp 210, such as a tungsten-halogen lamp from Avantes Inc., as the diffuse reflectance excitation source.

A laser line filter (available from Semrock, Inc.) is placed at the laser output to remove unwanted spontaneous emission that broadens the laser linewidth. An RG850 absorption filter is placed at the lamp output to reduce shorter wavelengths that may cause scatter within the spectrometer. The two beams are independently shuttered and combined using a MgF$_2$ plate at 45°, with the laser being transmitted and the white light source being reflected collinear. A photodiode placed at this intersection monitors the power of both sources. The light sources are focused through a small hole (4 mm dia.) in the paraboloidal mirror and delivered to the forearm 215 or a fused silica cuvette (1 cm pathlength) filled with the sample of interest. Achromatic doublets are used to shape the beams. The beam diameters at the sample are approximately 1 mm and the powers are 250 mW and 100 μW for the laser and white light source, respectively.

Back-scattered Raman light and diffuse reflectance are collected with the paraboloidal mirror and sent through a holographic notch filter (available from Kaiser Optical Systems, Inc.) to reduce the magnitude of the excitation peak. Specular reflection from the sample surface passes through the hole in the paraboloidal mirror and is significantly diminished. The collected light is then focused into a fiber bundle (FiberTech-RoMack LEONI Fiber Optics, Inc.) that transforms the circular shape of the collected light into a vertical line (~400 mm×26 mm) as illustrated in FIG. 9. The exit end of the fiber bundle serves as the entrance slit of a modified f/1.4 spectrometer 220 (available from Kaiser Optical Systems, Inc.). The light is dispersed by a holographic grating onto a 1300×1340 pixel liquid nitrogen-cooled CCD detector 225 (available from Princeton Instruments).

Considerable efforts are made to ensure instrument wavelength stability over time. Wavelength drift may be linear, in which all wavelengths shift the same amount, magnification-type, where pixels in different parts of the spectrum shift different amounts, or both may occur simultaneously. Our strategy is to detect and correct all variants of drift by measuring a stable reference material to an accuracy of ±0.3% for intensity and ±0.1 pixel for wavelength. Such performance has been achieved by using nine strong Raman peaks of acetaminophen powder as reference positions and monitored to within 0.01 pixels by spline fitting.

In the volunteer study, 17 non-diabetic human volunteers were recruited. Glucose tolerance protocol was followed and Raman spectra were acquired in the duration which the blood glucose concentration rises and falls. Reference glucose measurements were taken in a prescribed manner via finger stick, such as finger sticks available from Analox Instruments Ltd.

Figure 10A:
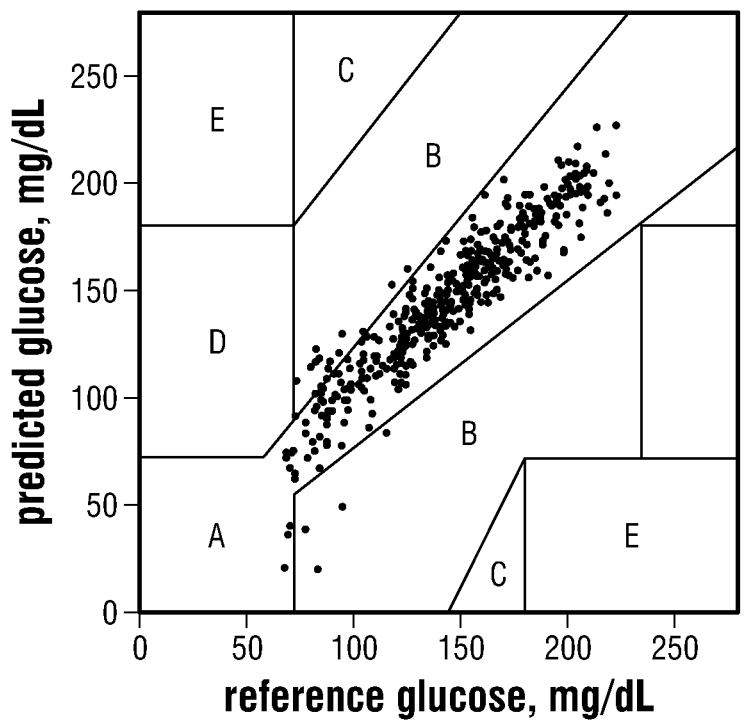
FIG. 10A shows predicted v. reference gluclose concentrations in human subjects.
Figure 10B:
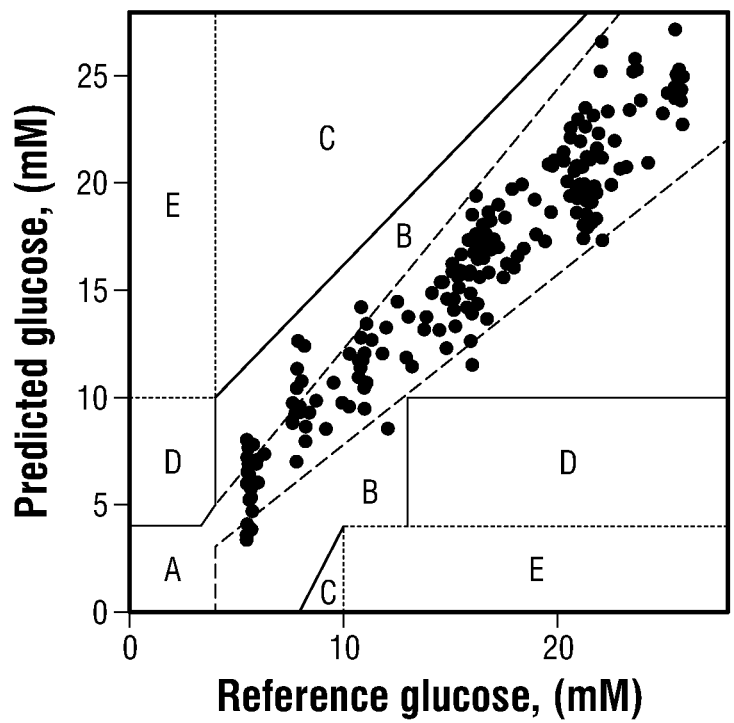
FIG. 10B shows predicted v. reference gluclose concentrations in a dog.

FIGS. 10A and 10B show predicted v. reference glucose concentrations in human subjects (FIG. 10A) and a dog (FIG. 10B). Using partial least squares (PLS) with leave-one-out analysis, the mean absolute errors for each volunteer were 7.8%±1.8% (mean±std) with $R^2$ values of 0.83±0.10, as shown in FIG. 10A. This type of Clarke error grid is used by physicians to evaluate the performance of non-invasive glucose techniques. Predictions falling in zones A and B are considered clinically acceptable. Spectral evidence indicating that glucose is an important part of the calibration was provided by analysis of the regression vectors.

Figure 11A:
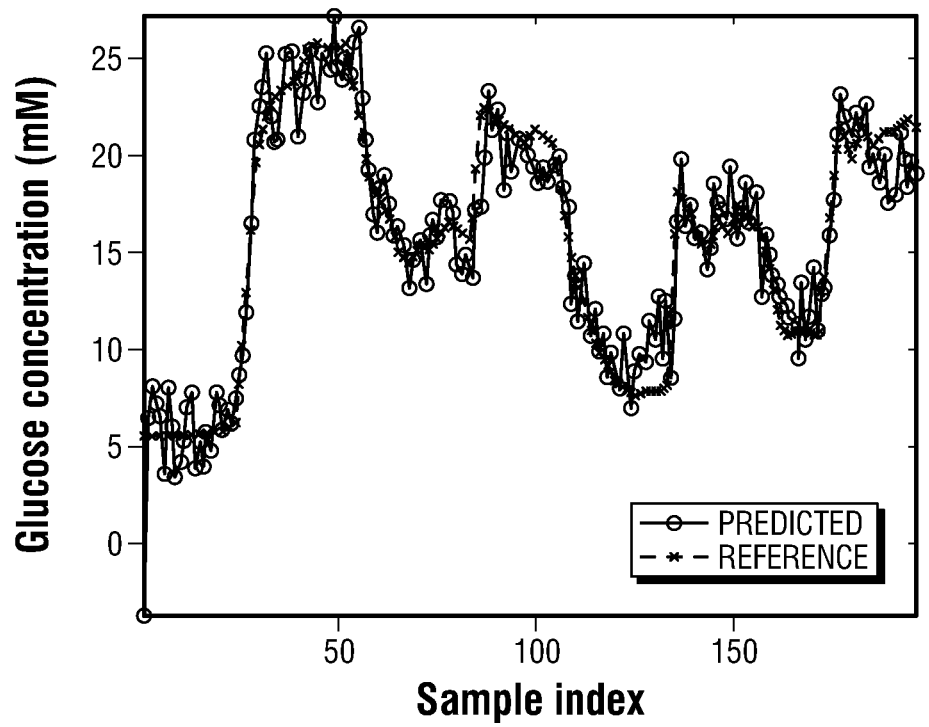
FIG. 11A shows the temporal tracking of the predicted versus the reference concentrations.
Figure 11B:
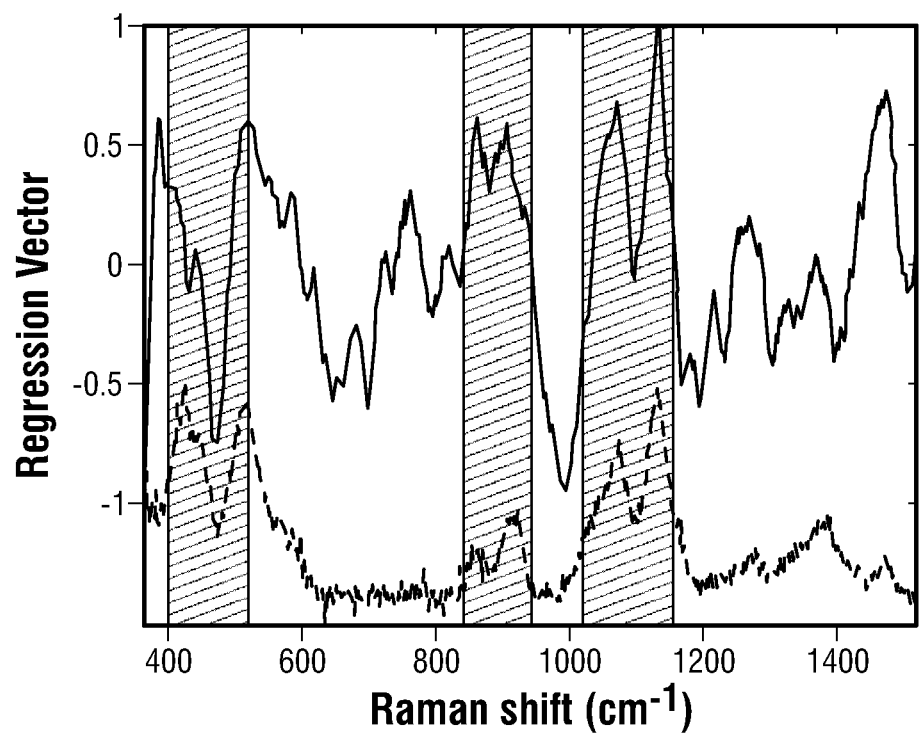
FIG. 11B shows regression vector and glucose Raman spectrum showing co-location of glucose peaks.

We have performed glucose clamping study on several dog subjects. This particular dog study was performed on a beagle anaesthetized for approximately 8 hours, during which its blood glucose concentration was clamped at 8 different levels within the range 5.6-25.6 mM (100-460 mg/dL). Each clamping level lasted for approximately 35 min. Raman spectra were acquired with an integration time of 1.8 seconds every 3.4 seconds. Reference glucose measurements were taken every 5 minutes via venous blood (Analox). Similar Clarke error grid was obtained and shown in FIG. 10B with standard error of prediction ~1.65 mM (29 mg/dL) and $R^2$=0.93. FIG. 11A shows the temporal tracking of the predicted versus the reference concentrations (~1.87 min between two samples). The regression vector and glucose Raman spectrum are plotted in FIG. 11B. The similarities between the two, specifically the co-location of all positive-going peaks, indicate that glucose was certainly measured. Randomized tests were carried out and the results showed no predictive capabilities with prediction errors greater than 135 mg/dL, further confirming that glucose was indeed measured.

RS and SERS for Neurotransmitter and Disease Biomarker Detection

For neurotransmitter measurements, studies based on spontaneous Raman or ultra-violet resonance enhanced Raman spectroscopy have been reported. These results demonstrate that Raman spectroscopy can provide excellent chemical specificity for different neurotransmitters.

As mentioned earlier, spontaneous Raman scattering is a very weak phenomenon, and thus has not been considered as a highly sensitive detection modality. While sub-mM errors have been demonstrated in concentration measurements in biological tissue and phantoms, better sensitivity in the range of sub-µM or even nM are necessary for neurotransmitter measurement in vivo. One solution to the sensitivity limitation is to employ "surface enhancement." It has been shown that orders of magnitude signal enhancement ($10^4$-$10^{14}$) can be achieved via surface enhancement, i.e., large signal boost when the molecules of interest are in the close proximity of a nanostructured surface made of noble metals such as gold or silver, such as the contacts with an array of gold pillars on the neural probe. The primary enhancing mechanism lies in that the incident laser light excites localized surface plasmon resonance on the metallic surface which in turn enhances the Raman scattering, and is thus called surface enhanced Raman scattering (SERS). Because SERS is a surface-specific technique, it precludes the possibility of entirely non-invasive measurement. However, unlike the noninvasive technique developed by the Dr. John C. Wolfe, the neural probe tip is actually in contact with various chemical substances, thus rationalizing using SERS.

In the literature, SERS has been applied to measure concentrations of neurotransmitters. An optical fiber with silver-coated and thinned tip has been employed to measure dopamine and other neurotransmitters. Recently, silver colloidal nanoparticles with a microscopy system were used to obtain spatial distribution of catecholamine at the single cellular level. SERS has also been applied to the detection of disease biomaker, e.g., it was recently demonstrated that SERS is capable of detecting amyloid β in the pico-Molar concentration range. Besides neurotransmitters, SERS has also been applied to detect vasopressin, a hormone released by the pituitary gland. We note that all the studies mentioned above were performed in vitro because a functional SERS neural/brain probe was not available. Neutral particle lithography has great potential in patterning large-area, dense, and robust nanostructures on non-planar surfaces, and is the approach we take.

RS for Molecular Diagnosis of Tissue Pathology

Figure 12A:
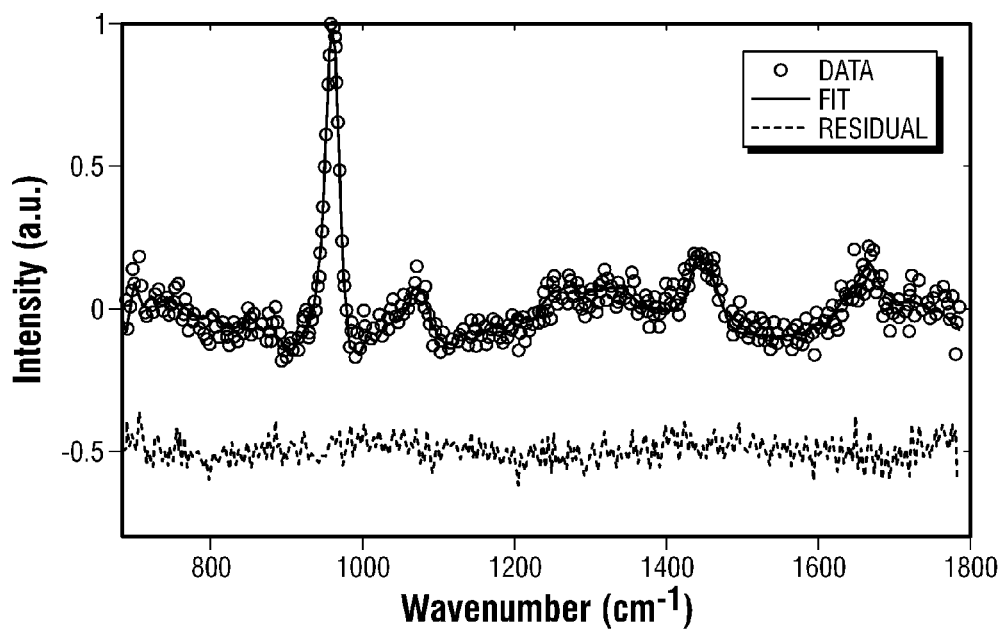
FIG. 12A shows the artery Raman spectrum collected with a fiber-optic probe.
Figure 12B:
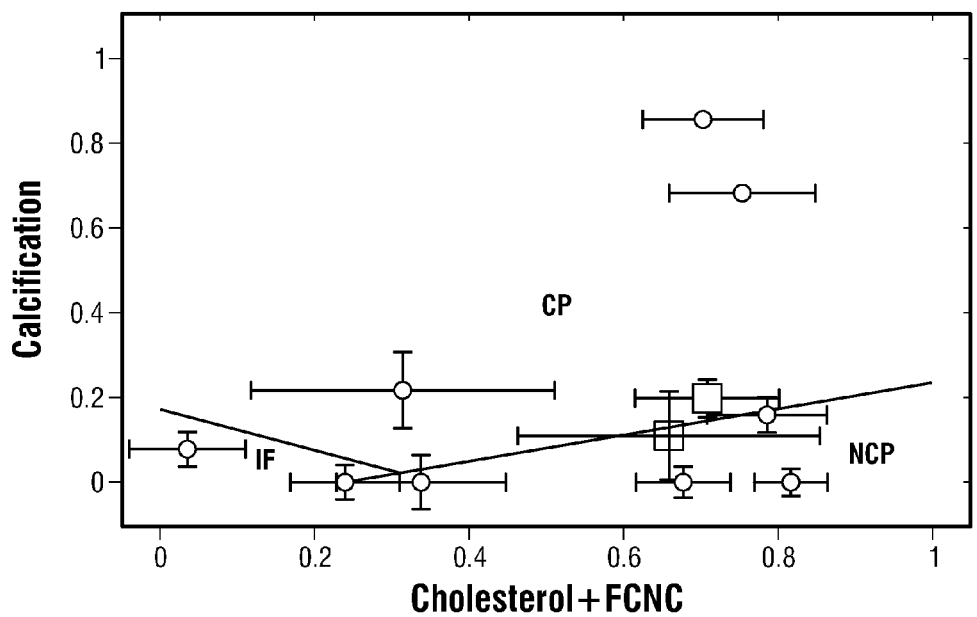
FIG. 12B shows diagnostic separation lines for calcified plaque (CP), non-calcified plaque (NCP), and intimal fibroplasia (IF)

In addition to concentration measurements in blood analytes, we demonstrated that RS is effective in differentiating diseased tissue from normal ones and provides diagnostic power in cardiovascular plaques. FIG. 12A shows the artery Raman spectrum collected with a fiber-optic probe together with the ordinary least squares fit using a morphological model previously developed by identifying prominent morphological structures in artery tissue and the corresponding Raman spectra using confocal Raman microscopy. FIG. 12B shows diagnostic separation lines for calcified plaque (CP), non-calcified plaque (NCP), and intimal fibroplasia (IF), together with confidence regions, using calcification and the sum of cholesterol and foam cell/necrotic core as the diagnostic parameters. Beside cardiovascular plaques, RS has also been applied to other disease pathology such as breast cancer diagnosis and margin detection, lung cancer pathology, and recently, in vivo brain function and brain tissue with the Alzheimer's disease.

Chemical-Specific Concentration Information Extraction

Figure 13:
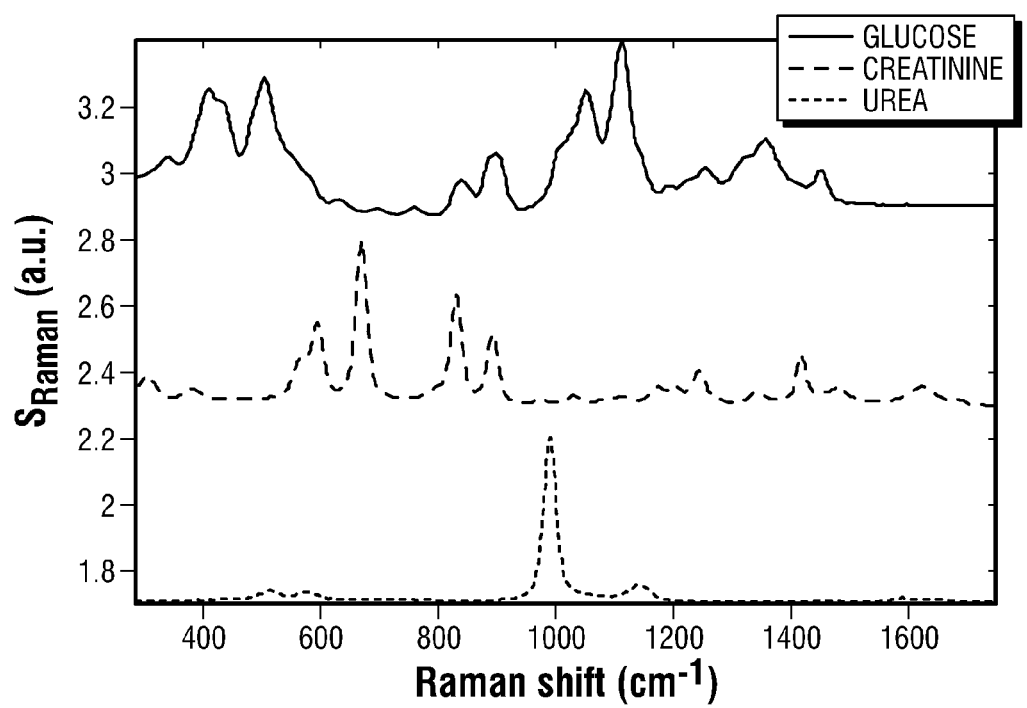
FIG. 13 shows Raman spectra of glucose (G), creatinine (C), and urea (U)

Owing to spectral overlap from various constituents in a complex biological system, traditional peak height (or area) measurement is inadequate. However, due to the nature of Raman spectra being very distinctive with sharp peaks, spectral "unmixing" is achievable via numerical modeling. As shown in FIG. 13, spectral overlap does exist among three example analytes: glucose, creatinine, and urea. However, each individual analyte has very distinctive Raman spectra because of the differences in their molecular structure. In this case, multivariate calibration can be employed as a powerful numerical modeling technique for extracting analyte concentration in complex chemical systems. When all of the individual constituent spectra are not known, implicit calibration methods are often adopted. Principal component regression (PCR) and partial least squares (PLS) are two frequently used methods. Recently, we developed a novel hybrid algorithm, i.e., combining features of implicit and explicit methods, called "constrained regularization", and obtained superior results compared to PLS and another hybrid method, hybrid linear analysis (HLA).

Figure 14A:
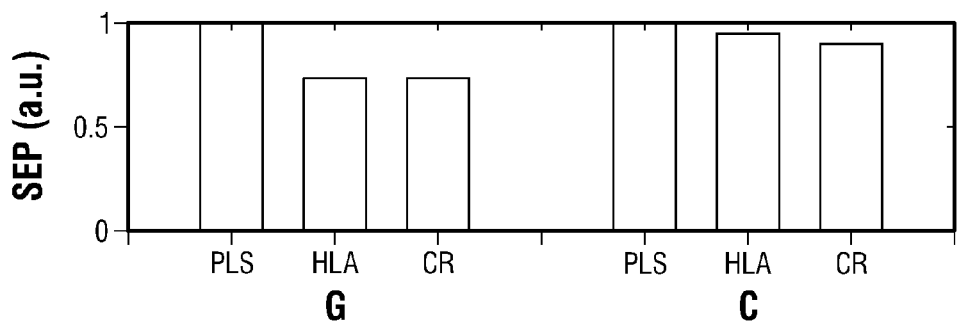
FIG. 14A to 14C shows the standard error of prediction (SEP) of component regression (CR), partial least squares (PLS), and hybrid linear analysis (HLA) in uncorrelated analyte concentrations, correlated analyte concentrations, and turbid media.
Figure 14B:
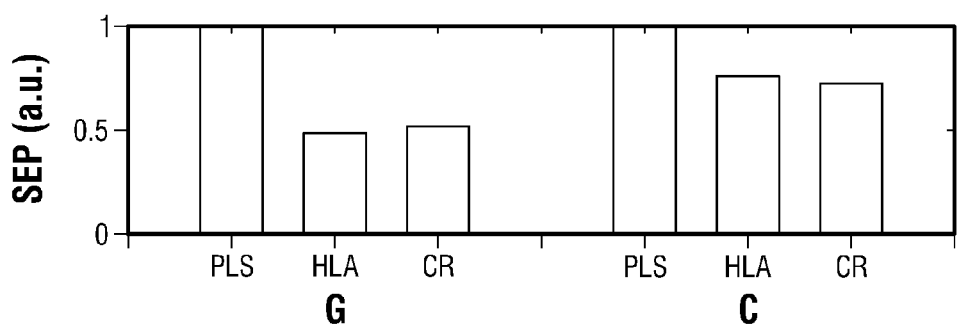
Figure 14C:
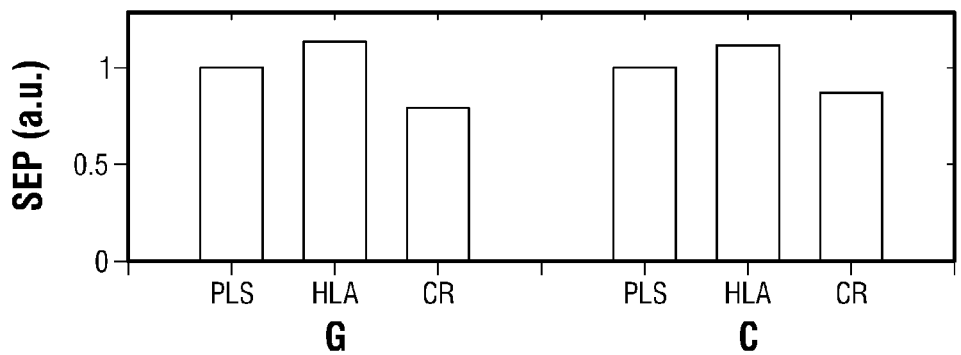

FIGS. 14A-14C show the advantages of CR over PLS and HLA in various scenarios: uncorrelated analyte concentrations, correlated analyte concentrations, and turbid media. Samples were made of water solution with three analytes, glucose, creatinine, urea, in either random or correlated concentrations. In the turbid samples, intralipid and India ink were employed to introduce scattering and absorption variations, respectively. The correlated analyte concentration experiment was to simulate analyte covariations, a common source of error in multivariate calibration. The turbid experiment was to simulate biological tissue such as skin, and to address the fact that turbidity can vary from site to site. Standard error of prediction (SEP) is used as a metric to compare different calibration methods. Normalizing to the SEP of PLS, it is observed that in all cases CR outperforms PLS, indicating that CR provides more accurate results than PLS because of the incorporation of the glucose spectrum. In addition, CR performs far better than PLS when there are analyte covariations. Compared to HLA, which also incorporates the target spectrum, CR performs similarly in clear solution samples. However, CR performs significantly better than HLA in turbid samples, indicating CR is more robust than HLA because CR incorporates the target spectrum via a flexible fashion. Both CR and PLS will be employed to extract chemical-specific information from the spectroscopic measurements.

Technology Suite for Nanolithography on Non-Planar Surfaces

Neutral Particle Proximity Lithography for the Elimination of Charging Artifacts in Ion Beam Lithography Proximity ion beam lithography (IBL) is a technique where a broad, collimated beam of energetic light ions (e.g. 10-100 keV $Li^+$, $H^+$, and $He^+$) floods a stencil mask and the transmitted beamlets transfer the mask pattern to resist on a substrate. Very high throughput is possible since the entire mask is printed at one time. Moreover, femtometer particle wavelengths permit diffraction free nanoscale printing over practical proximity gaps. Thus, nanoscale resolution and the potential for high throughput make IBL a promising approach for nanomanufacturing. This has been explored in several pilot studies involving patterned magnetic recording media, high-frequency surface acoustic wave filters, integrated circuits on spherical substrates, and metal mesh optical components.

Ideally, ions travel in straight lines through vacuum casting a crisp shadow of the mask onto the substrate blurred only by the penumbra of the source, scattering in the mask, and Fresnel diffraction. In practice, however, the ion beamlets transmitted by the mask can be distorted by ambient electromagnetic fields and by transient charge that builds up on insulating substrates and ungrounded mask surfaces. This is not surprising as the aspect ratio of a beamlet can approach 50,000:1 in large depth-of-field applications. However, note that IBL may be utilized to manufacture the neural probe discussed herein if the metallic traces and/or probe are properly sized to account for such mask distortions. We showed that these charging artifacts can be completely eliminated by neutralizing the lithography ions by charge transfer scattering before they reach the mask. Penumbra and diffraction are unchanged since the neutralization process, where an energetic ion captures an electron from a thermal neutral particle, accurately preserves both the direction and energy of the incident ions. Moreover, since ions are neutralized within the first few angstroms of a solid, ions and neutral atoms with the same energy and nuclear charge have identical interactions with the mask and resist. Thus, neutral particle lithography (NPL) achieves the ideal IBL image by removing all charging artifacts, thereby allowing the size of a neural probe and/or metallic traces on the probe to be minimized.

Figure 15A:
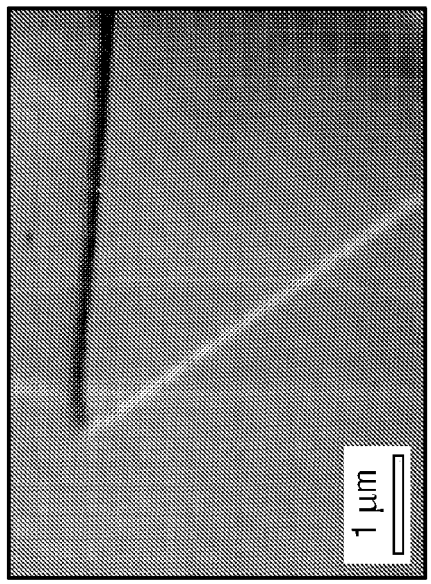
FIG. 15A shows micron-scale line-edge roughness (LER) in an IBL image on PMMA resist on a quartz photomask blank.
Figure 15B:
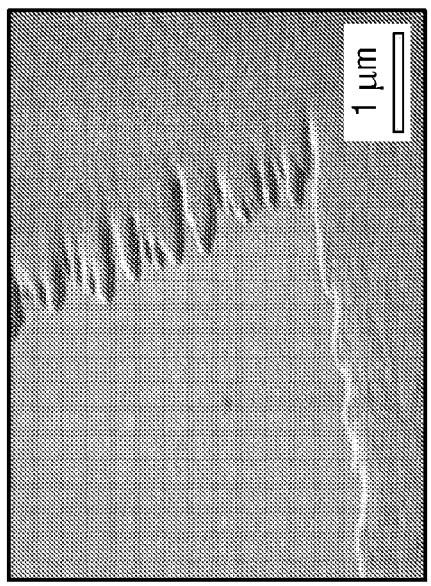
FIG. 15B shows a NPL print where the LER is entirely absent.

We compared NPL and IBL exposures on an insulating substrates. FIG. 15A shows micron-scale line-edge roughness (LER) in an IBL image on PMMA resist on a quartz photomask blank. FIG. 15B shows the corresponding NPL print where the LER is entirely absent. Charge build-up on the photomask blank during exposure causes severe distortion of the ion beamlets. Secondary electron emission should create a similar charge distribution during neutral particle exposures, but neutral particles are intrinsically immune to this charge.

Figure 16A:
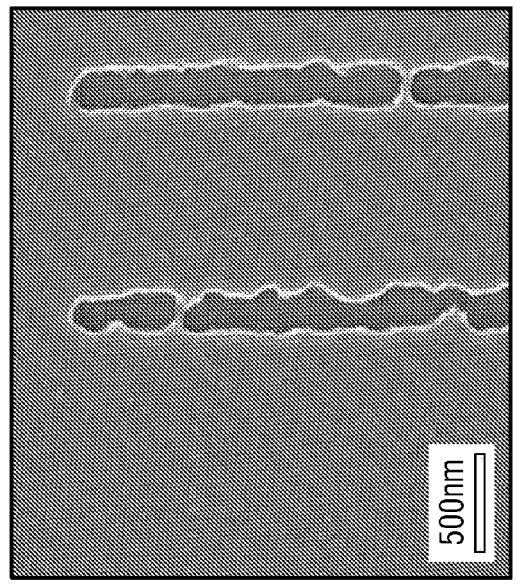
FIG. 16A shows a NPL image for a 1.13 mm mask-to-wafer gap.
Figure 16B:
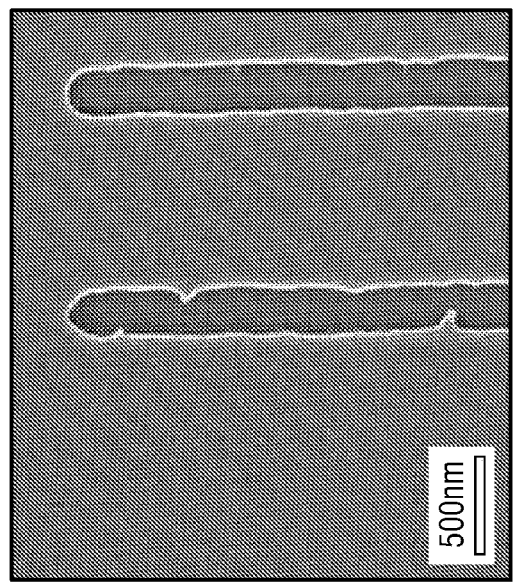
FIG. 16B shows a IBL print for a 1.13 mm mask-to-wafer gap.
Figure 17A:
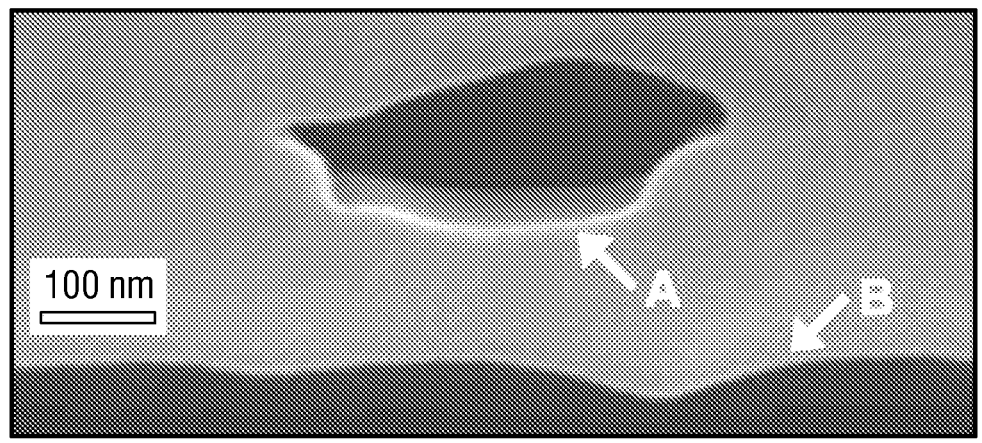
FIG. 17A-17C show, respectively, the mask, NPL print, and IBL print for a nanoscale fish-shaped mask defect.
Figure 17B:
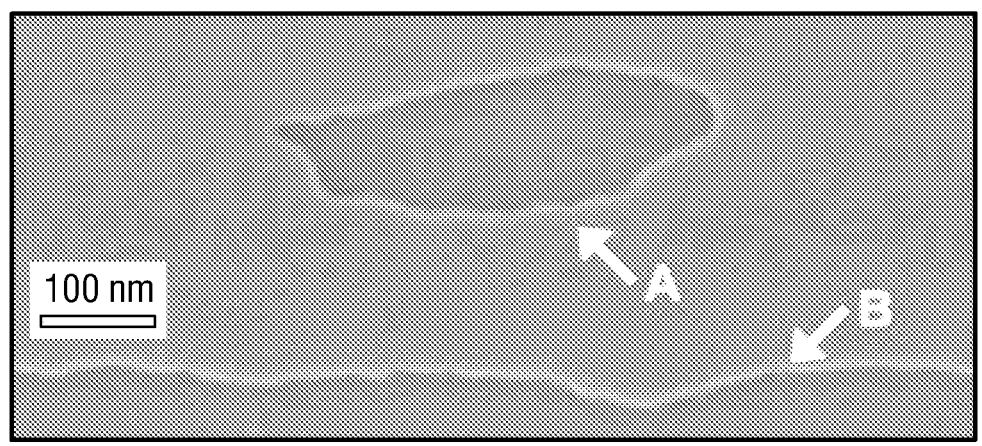
Figure 17C:
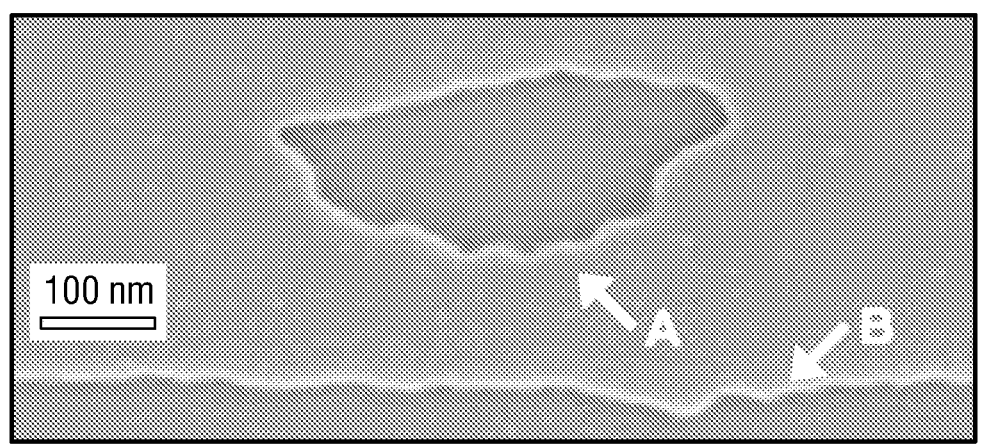

We also compared line edge roughness in IBL and NPL images on conducting silicon substrates using a nominally conducting silicon mask. A 100 nm thick PMMA resist layer was exposed with 30 keV particles, sufficient to discharge the surface to the substrate by particle-induced conductivity. The NPL image for a 1.13 mm mask-to-wafer gap is shown in FIG. 16A. The protrusions on the edges of the line are shadows cast by solid obstructions on the walls of the mask windows. These obstructions, which cannot be seen in micrographs of either mask face, presumably reside in the mask interior. Protrusions are also seen in the IBL print for the same gap shown in FIG. 16B, but they are larger, more irregular, and, in two cases, have resulted in bridging of the lines. The IBL print shows line edge roughness and bridging due to charging of the mask sidewall. Since the roughness increases in proportion to the proximity gap, ion deflection by mask charge must be the cause. The origin of these insulating obstructions may be intrinsic to the mask etching process or they may be insulating deposits formed by particle-induced deposition from oils in the exposure chamber. The fact that they cannot be seen from the mask face implies that applying a conducting film may be quite challenging. NPL provides a simple solution without the need for a conducting coating. FIG. 17A-17C show, respectively, the mask, NPL print, and IBL print for a nanoscale fish-shaped mask defect. The IBL print is much less well defined and, again, has significantly larger roughness than the NPL print.

Fabrication of Nanoscale Masks

Figure 18A:
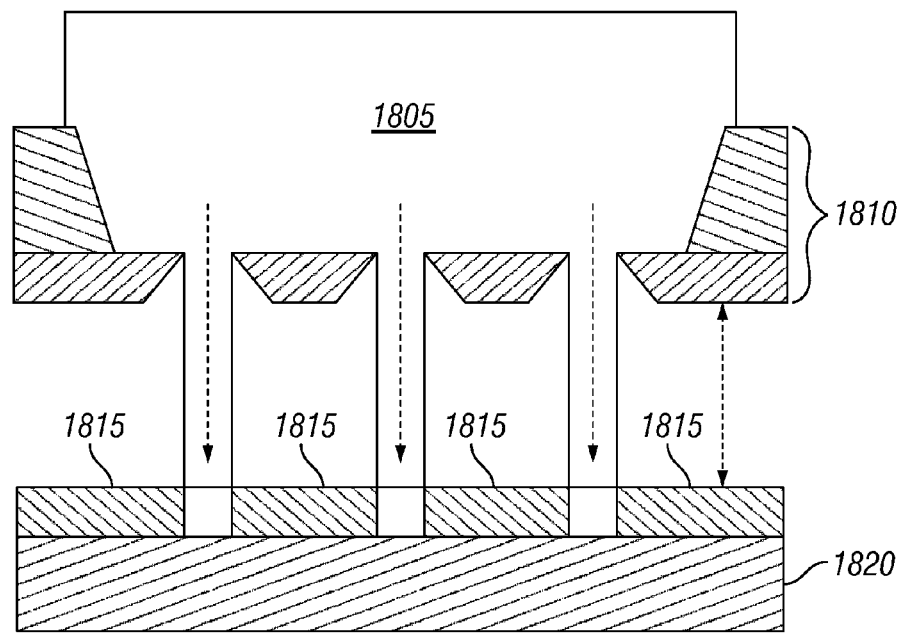
FIG. 18A is an illustrative implementation of a mask schematic.

Mask membranes are flat on the front and recessed inside a 0.5 mm thick integral support frame on the back, as shown in FIG. 18A. Lithography and etching are carried out from the front of the mask which faces the substrate during proximity lithography. Thus, the size and roughness of a printed feature are defined by the opening on the back of the mask. To prevent particle scattering from sides of the mask opening they should flare from back-to-front. Broad beam exposure of $He^0$ particles 1805 pass through a patterned mask 1810 that is at a fixed proximity gap (10-100 μm) from resist 1815 and substrate 1820.

Figure 18B:
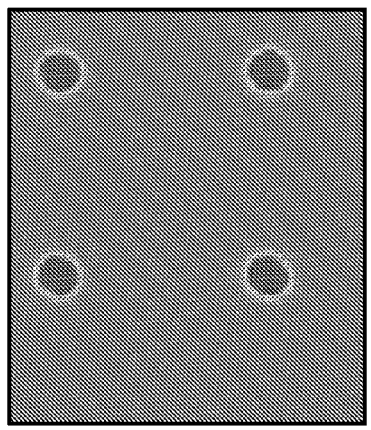
FIG. 18B shows 74.5 nm openings in the back of a mask.

A mask with arrays of 74.5 nm diameter on 400 nm pitch was fabricated using 100 nm thick $SiO_2$ hard mask deposited on a 350 nm thick, 1×1 $cm^2$, silicon membrane. A 300 nm thick PMMA resist layer was then applied and patterned by electron beam lithography with cold development at 0° C. These patterns were transferred into the hard mask by $C_4F_8$-reactive ion etching (RIE) and through the membrane by HBr-RIE. FIG. 18B shows the back of the mask in a region where the average diameter of the openings is 74.5 nm. The nominal diameter of the resist mask openings in this region was 100 nm implying an average wall angle of ~36 mrad.

Controlling Image Noise

Figure 18C:
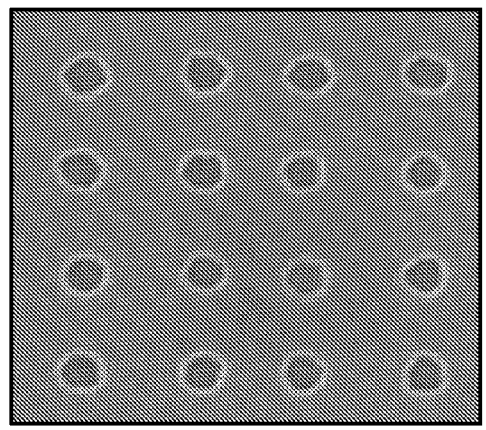
FIG. 18C shows an NPL print of 4 mask images offset by half the mask pitch.
Figure 19A:
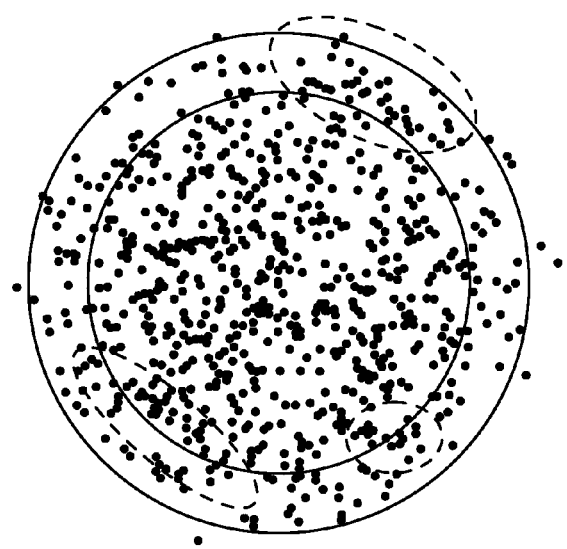
FIG. 19A shows a random array of particle landing points on the resist surface.
Figure 19B:
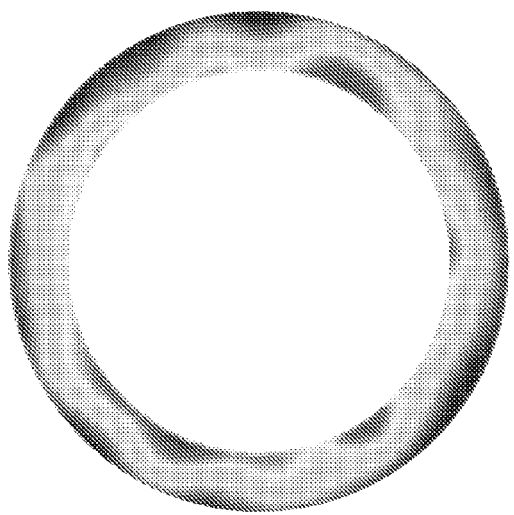
FIG. 19B shows energy density fluctuation above and below the development threshold.
Figure 19C:
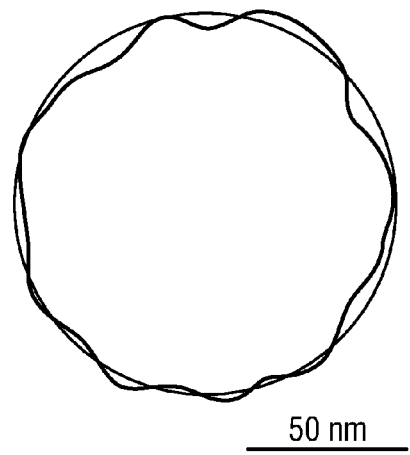
FIG. 19C shows roughness in the printed image.
Figure 20A:
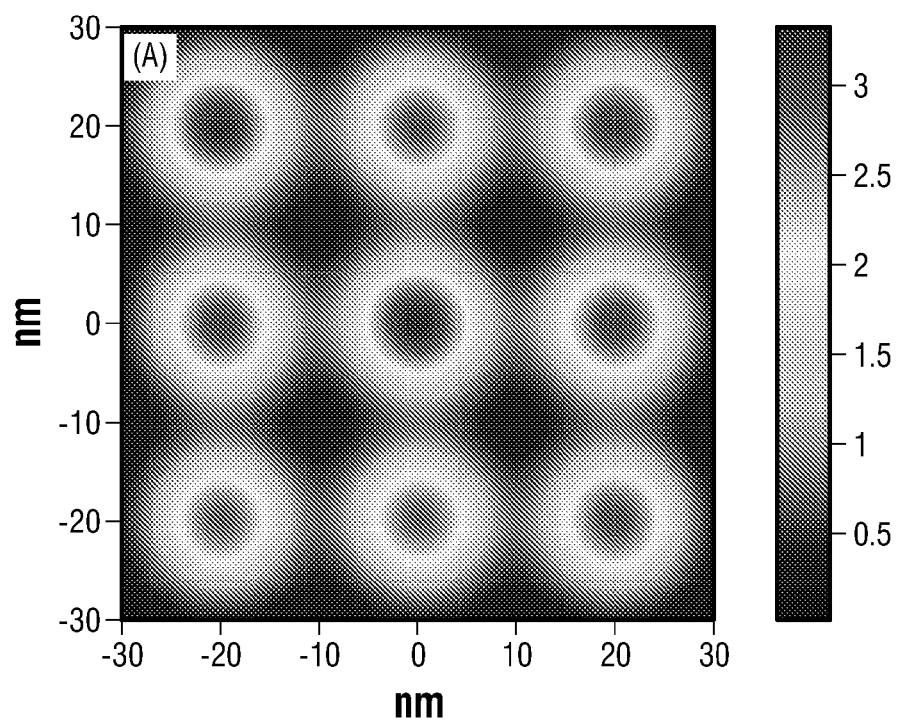
FIG. 20A shows the resulting energy distribution.
Figure 20B:
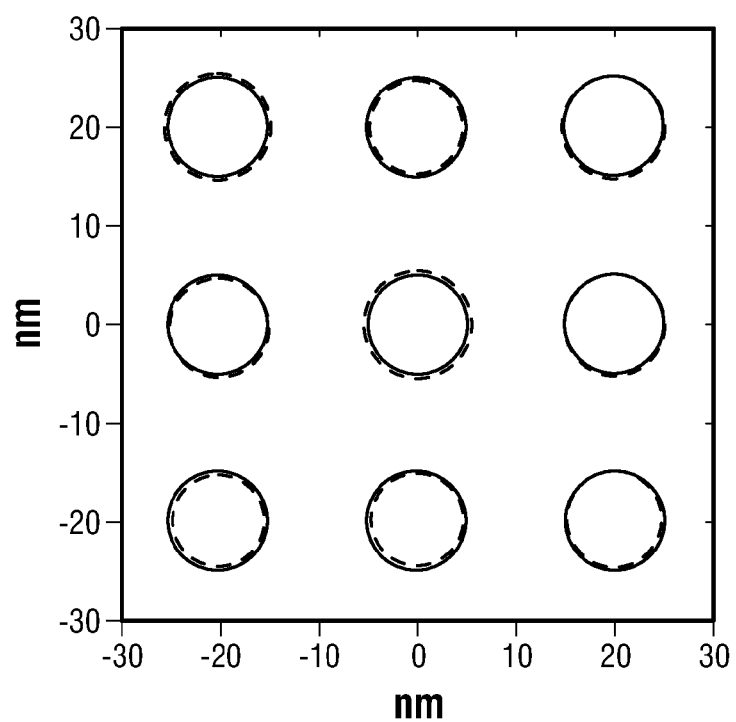
FIG. 20B shows the developed contours.

A distinctive feature of resist exposure by energetic helium ions or neutral atoms is that critical exposure densities are very low, about 100 times smaller than for electrons. Thus, particle distributions are sparse, leading to significant statistical fluctuations in the energy density even in Polymethylmethacrylate (PMMA), a relatively insensitive, non-chemically amplified resist. This is seen in FIG. 18A-18C where the mask was printed 4 times offset by half the mask pitch. Thus, the sets of dots printed in each of the four quadrants were printed with exactly the same mask opening; thus, the noise in the image is statistical in nature. We conducted an integrated study of image noise in helium lithography that compares shape variations in neutral particle mask images with the predictions of a Monte-Carlo model. The model accounts for the following: 1) the Poisson statistics of the particle emission process (shot noise), 2) the random distribution of particle landing positions on the resist surface, 3) the random particle trajectories in the resist, and 4) smoothing of the deposited energy distribution by exposure and development processes. Proximity lithography experiments were carried out using 10 keV neutral helium atoms in 20 nm thick Poly(methyl-methacrylate) resist under conditions of 12.7 nm [FWHM] penumbral image blur. The energy smoothing function is assumed, based on previous experiments, to be Gaussian and its standard deviation σ treated as a free parameter. Model predictions of the power spectral density of line edge roughness agree with experiment for σ=5.0±0.5 nm. FIG. 19A shows a random array of particle landing points on the resist surface. Particle bunching (circled) in the region of partial exposure, bounded by the red circles, on the edge of the pattern causes the energy density to fluctuate above and below the development threshold as shown in FIG. 19B. This, in turn, results in roughness in the printed image as shown in FIG. 19C. The model predicts that using a resist with a critical dose 20 times higher than PMMA and reducing penumbra to 0.5 nm [FWHM] would reduce shape fluctuations to less than 0.5 nm [FWHM] for dense 10 nm dot arrays. FIG. 20A shows the resulting energy distribution, and FIG. 20B shows the developed contours. The conclusion of these studies is that the suppression of image noise in high resolution neutral particle (or ion) prints requires both very insensitive resist and very small penumbral blur. We describe, in the following section the printer that we developed to satisfy these demanding requirements.

Development of a High Throughput Neutral Particle Lithography Tool

The source parameter that determines the relationship between current density, aerial image blur, and proximity gap in NPL is the source brightness, which for a Gaussian source is given by $\beta=I_\Omega/2\pi\sigma^2$, where $I_\Omega$ angular emission density and σ is the standard deviation. The flux density ī on the wafer is given by $\bar{i}=2\pi\beta(\sigma'/g)^2$, where σ' is the standard deviation of aerial image blur and g is the gap between the mask and the wafer.

Figure 21:
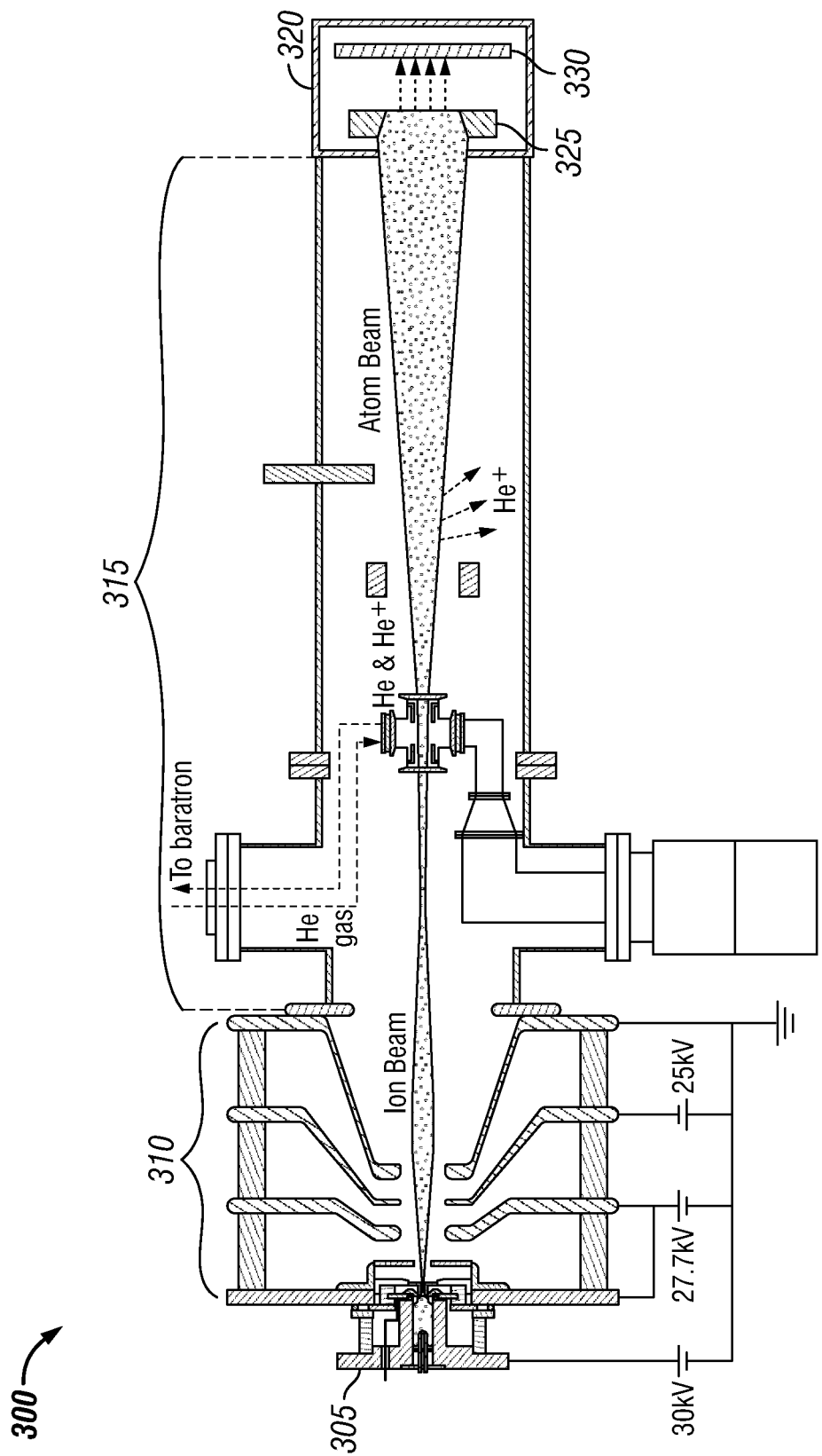
FIG. 21 is an illustrative implementation of a neutral particle lithography tool.

FIG. 21 shows the apparatus 300 built for an MRI project similar to the device discussed in U.S. Pat. No. 7,504,619 to Wolfe et al. Helium ions are extracted from a multicusp source 305, accelerated and focused by a 3-element electrostatic lens 310 toward the optical axis. Space charge repulsion in this high current beam prevents the formation of a true cross-over; instead, it converges to a waist of minimum diameter, then diverges downstream. The ions are neutralized by charge transfer scattering in a differentially pumped, high pressure cell 315 charged with thermal helium gas. Residual ions are removed with an electrostatic deflector and a pure beam of eneretic neutral helium atoms drifts toward the exposure chamber 320, which contains mask 325 and substrate 330.

Typically, the source operates at a pressure of 8 mtorr a discharge power of 360 W. Experimental knife-edge data shows that the asymptotic rays far from the beam waist appear to emanate from a virtual source with a Gaussian emission profile whose diameter and brightness are 82±10 μm [2σ] and 1,068 A/cm$^2$-sr (6.7*10$^{21}$ particles/sec-cm$^2$-sr), respectively. This leads to the important conclusion that the space charge region is equivalent to a diverging lens that can form a very small virtual source.

The total conversion efficiency, increases linearly ($R^2$=0.998) from 11% at a helium cell pressure 0.5 mtorr to 82% at 7.5 mtorr, saturating near 87% above 10 mtorr. The diameter (2σ) of the neutral source increases linearly ($R^2$=0.96) over this pressure range from 0.19 mm to 0.25 mm, between 2.3 and 3.0 times larger than that of the virtual ion source. The peak brightness 1.9*10$^{21}$ particles/cm$^2$-sr, occurs for a cell pressure of 7.7 mtorr. We conclude that cell pressure can be used to modulate the beam current with only minor changes in source size, hence, lithographic blur. This is important to the present design since modulating the current of the parent ion source would drastically change the characteristics of the space charge lens. The brightness formula implies that the exposure time for PMMA would be about 16 seconds for σ'=5 nm, appropriate for 50 nm printing, and g=0.5 mm.

Nanoscale Pattern Definition on Non-Planar Surfaces

Figure 22A:
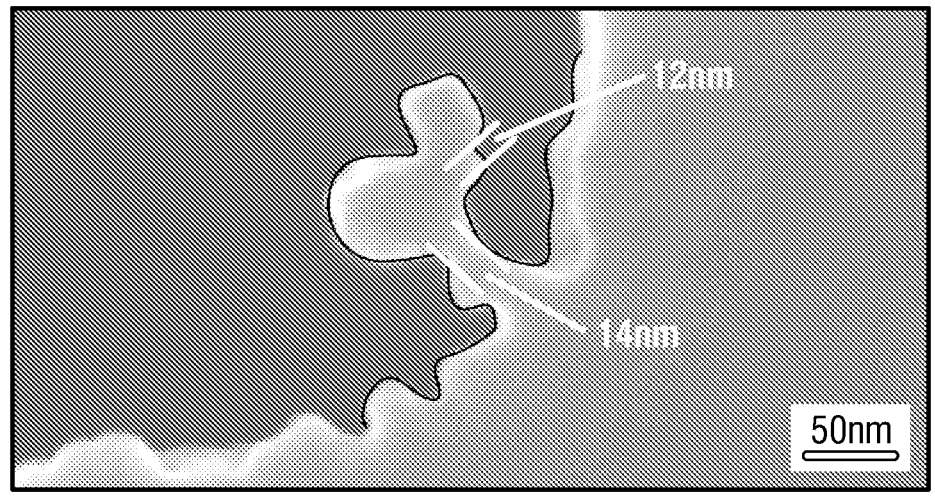
FIG. 22A shows a mask.
Figure 22B:
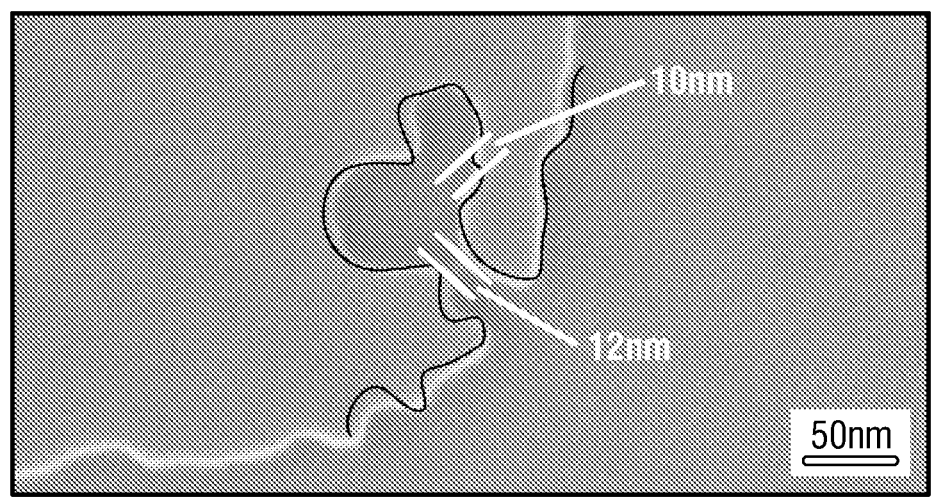
FIG. 22B shows a print of a mask defect using a NPL tool.

We have just seen that the MRI printer in FIG. 21, meets the challenge of fabricating low noise, nanoscale images with a staggering proximity gap. We have developed a conformal, plasma deposited resist to complement this capability. The critical exposure dose is about 16 times larger than PMMA, almost exactly what is required for the low noise imaging discussed above. FIG. 22A shows a mask, and FIG. 22B shows a print of a mask defect in this resist ~10 nm resolution and ~2 nm pattern fidelity. There is no noise in the image.

SUMMARY

Figure 23:
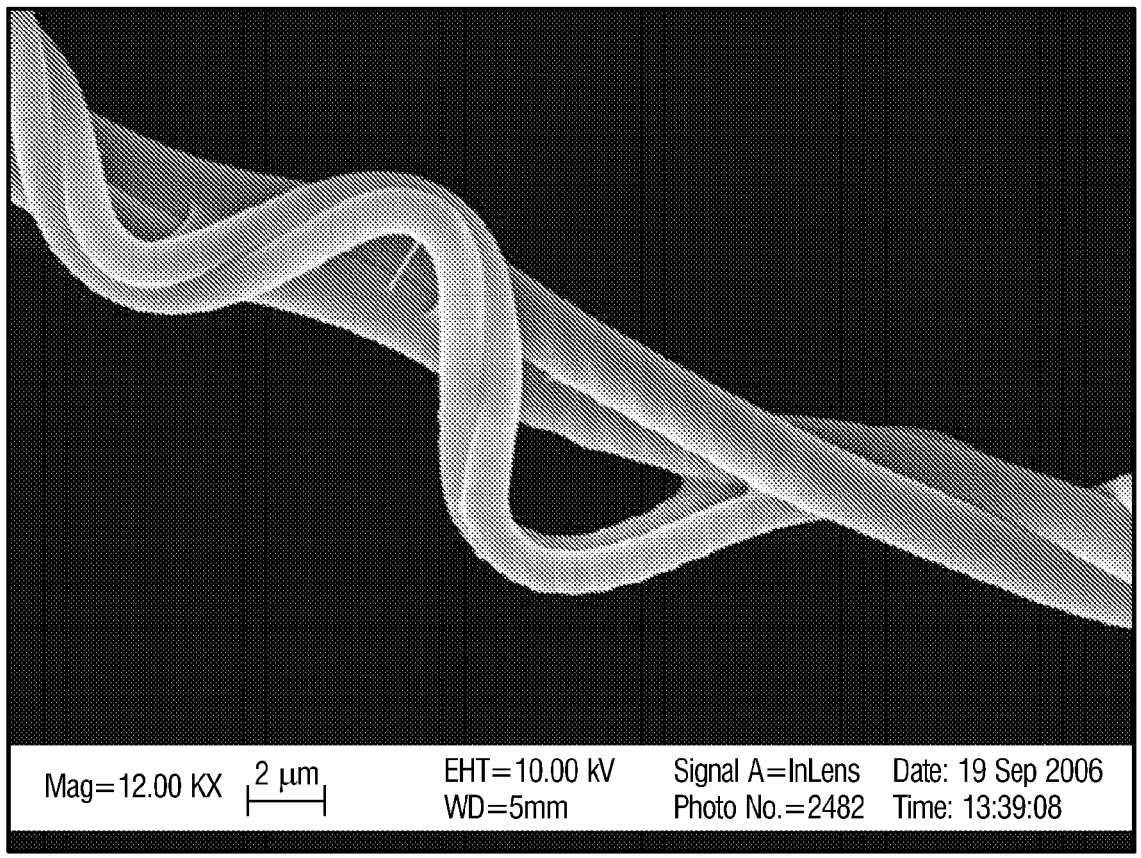
FIG. 23 shows the capability of a NPL tool.

FIG. 23 shows a line-space pattern with 1 μm pitch printed in plasma deposited resist on a spider's web. FIG. 23 summarizes the capability of the non-planar lithography technology suite: Noise-free 500 nm lines and spaces have been printed in plasma deposited resist on a spider's web; the substrate was insulating and non-planar, the proximity gap was 1 cm, and there is no image noise. Moreover, each large-field exposure takes just 4.5 minutes.

In a first illustrative implementation, a neural probe of circular cross-section provides a narrow tapering tip, incorporating at least one integrated sensing element to measure neural activity in the brain, the spinal cord, or other neural bundles in animals and humans. A method for fabricating a neural probe may involve a probe substrate is a tapered needle fabricated from the shape memory alloy known by the tradename of Nitinol. Further, ion and/or neutral particle proximity lithography may be utilized to form a desired pattern on the probe. The ion/or neutral particle proximity lithography may use a conformal resist formed by plasma enhanced chemical vapor deposition.

In another illustrative implementation, a neural probe of circular cross-section provides a narrow tapering tip, incorporating sensing elements comprising at least one microelectrode for sensing action potentials due to the firing of nerves near the probe tip or along its length. Each microelectrode shall comprise an insulated metal line formed on the side of the probe with an uninsulated portion at the terminus to enable electrical contact with the cerebro-spinal fluid. An un-insulated portion of the neural probe may have a nanostructured coating to reduce the electrical contact resistance between the probe and the cerebro-spinal fluid.

In another illustrative implementation, a neural probe of circular cross-section provides a narrow tapering tip, incorporating sensing elements comprising at least one Raman scattering sensor for detection the biochemical changes induced by neural activity near the probe tip or along its length by Raman scattering. Each Raman scattering sensor comprises a lightguide, with a region of lower index of refraction coating a region of higher index, for guiding exciting laser light to the sensing region and returning Raman scattered light to a detector outside the body, with an uncoated portion at the terminus to enable the interaction of laser light with the local biochemical microenvironment. The uncoated portion of the neural probe may have a nanostructured metal coating to enhance the Raman signal through the surface enhanced Raman scattering effect. The regions of higher index and lower index of the neural probe may be formed by plasma enhanced chemical vapor deposition.

In another illustrative implementation, a neural probe contains at least one microelectrode and one Raman scattering sensor. The regions of higher index and lower index of the neural probe may be formed by a dip coating process using spin-on dielectrics.

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure.

PUBLICATIONS

1. V. Parekh, A. Ruiz, P. Ruchhoeft, H. Nounu, D. Litvinov, and J. C. Wolfe, "Estimation of scattered particle exposure in ion beam aperture array lithography," J. Vac. Sci. Technol. B 24,2915 (2006).

2. B. Craver, A. Roy, H. Nounu, and 1. C. Wolfe, "Mechanical nanostepping for atom beam lithography," J. Vac. Sci. Technol. B 25(6), 2192-2194 (2007).

3. Hong-jie Guo, Barry Craver, Jackson Reynolds, and John C. Wolfe, "Design studies for a high brightness, energetic neutral atom source for proximity lithography," J. Vac. Sci. Technol. B 25(6), 2188-2191 (2007).

4. L. Xu, N. Sadeghi, V. M. Donnelly, and D. J. Economou, "Nickel atom and ion densities in an inductively coupled plasma with an internal coil", Journal of Applied Physics, p. 013304, vol. 101, (2007).

5. (Invited Review) J. C. Wolfe and B. P. Craver, "Neutral Particle Lithography: A simple solution to charge related artifacts in ion beam proximity printing, "Journal of Physics D, Vol. 41, pp. 024007-024018, January 2008.

6. Dhara Parikh, Barry Craver, Hatem Nounu, Fu-on Fong, and John C. Wolfe, "Nanoscale pattern definition on non-planar surfaces using ion beam proximity lithography and conformal, plasmadeposited resist, Journ. Microelectromechanical Systems, Vol. 17, pp. 735-740, June 2008.

7. Barry Craver, Hatem Nounu, James Wasson, and John C. Wolfe, "Neutral particle proximity lithography: Non-contact nanoscale printing without charge-related artifacts, "J. Vac. Sci. Technol. B, Vol. 26, pp. 1866-1870, November 2008.

8. D. 1. Economou, "Fast (lOs-100s eV) Neutral Beams for Materials Processingll, Journal of Physics D: Applied Physics, p. 024001, vol. 41, (2008).

9. Lin Xu, Azeem Nasrullah, Zhiying Chen, Manish Jain, Demetre J. Economou, Paul Ruchhoeft, and Vincent M. Donnelly, "Etching of nanopatterns in silicon using nanopantographyll, Applied Physics Letters, p. 013124, vol. 92, (2008).

10. Ananya Roy, Leonidas Ocola and J. C. Wolfe, "Image Noise in Helium Lithography," accepted, Journ. Vac. Sci. Technology (2009).

11. Hong-jie Guo, Ananya Roy, Leonidas E. Ocola, and J. C. Wolfe, "A point source of energetic helium atoms for proximity lithography," in preparation based on work presented at EIBPN09, Marco Island, Fla. May 26-29 (2009).

12. Ananya Roy, Barry Craver, Hongjie Guo, Leonidas E. Ocola, and J. C. Wolfe, "Determination of internal resist blur from the power spectrum of line edge roughness" in preparation based on work presented at EIBPN09, Marco Island, Fla. May 26-29 (2009).

What is claimed is the following:

1. A method for manufacturing a neural probe comprising the steps of:
   forming a neural probe, wherein a tip of the neural probe is tapered;
   coating the neural probe with a first coating to form a first cladding layer, wherein the first cladding layer insulates the neural probe;
   coating the first cladding layer with a metal layer;
   coating the metal with a first resist layer;
   aligning a stencil mask with the neural probe and exposing the first resist layer to form a mask pattern, wherein first unexposed resist is removed with a developer;
   removed unmasked metal with an etchant, wherein unremoved metal forms one or more metallic trances along the neutral probe;
   coating the neural probe with a second resist coating to form a second cladding layer; and
   aligning a first fine wire mask with the probe and exposing the second resist coating, wherein second unexposed resist is removed with a developer to reveal a portion of the metallic traces, and the exposed portion of the metallic traces forms one or more contacts.

2. The method of claim 1, wherein the mask pattern is formed using neutral particle lithography (NPL) or ion beam lithography (IBL).

3. The method of claim 1, wherein the first cladding layer and the second cladding layer are plasma polymerized methylmethacrylate (PPMMA), poly(methylmethacrylate) (PMMA), glass or thermoplastic.

4. The method of claim 1, wherein the first cladding layer and the second cladding layer are formed by plasma enhanced chemical vapor deposition or a dip coating process using spin-on dielectrics.

5. The method of claim 1, wherein the first cladding layer has a lower refractive index than the core.

6. The method of claim 1, wherein the metal is gold.

7. The method of claim 1, wherein the probe is formed from a thin, rigid material.

8. The method of claim 1, wherein the probe is formed from a shape memory alloy, stainless steel, titanium, glass fiber, or optical fiber.

9. The method of claim 1, further comprising aligning a second fine wire mask and exposing the second resist coating prior to removal of the second unexposed resist, wherein the second fine wire mask is orthogonal to the first fine wire mask.

10. The method of claim 1, further comprising coating the neural probe with a core material after the metallic traces are formed to form a core layer.

11. The method of claim 1, wherein the core material is silicon or silica.

12. The method of claim 1, further comprising forming a vertical array of metallic pillars on the one or more contacts, wherein the metallic pillars are nanosized.

13. The method of claim 12, wherein the vertical array of metallic pillars are gold.

14. The method of claim 12, wherein the vertical array of metallic pillars are formed by nanolithography.

* * * * *